(12) United States Patent
Steinke et al.

(10) Patent No.: US 10,576,269 B2
(45) Date of Patent: Mar. 3, 2020

(54) FORCE-DECOUPLED AND STRAIN RELIEVING LEAD AND METHODS OF MAKING AND USING

(71) Applicant: Boston Scientific Neuromodulation Corporation, Valencia, CA (US)

(72) Inventors: G. Karl Steinke, Valencia, CA (US); Michael X. Govea, Castaic, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 189 days.

(21) Appl. No.: 15/859,136

(22) Filed: Dec. 29, 2017

(65) Prior Publication Data

US 2018/0185633 A1 Jul. 5, 2018

Related U.S. Application Data

(60) Provisional application No. 62/441,948, filed on Jan. 3, 2017.

(51) Int. Cl.
*A61N 1/05* (2006.01)
*A61N 1/36* (2006.01)
(Continued)

(52) U.S. Cl.
CPC ....... *A61N 1/0534* (2013.01); *A61N 1/36071* (2013.01); *A61N 1/37217* (2013.01);
(Continued)

(58) Field of Classification Search
CPC ............. A61N 1/0534; A61N 1/36071; A61N 1/37217; A61N 1/0539; A61N 1/0551;
(Continued)

(56) References Cited

U.S. PATENT DOCUMENTS 4,602,624 A 7/1986 Naples et al.
4,630,611 A 12/1986 King
(Continued)

FOREIGN PATENT DOCUMENTS

EP 0580928 A1 2/1994
EP 0650694 B1 7/1998
(Continued)

*Primary Examiner* — Catherine M Voorhees
(74) *Attorney, Agent, or Firm* — Lowe Graham Jones PLLC; Bruce E. Black

(57) ABSTRACT

An electrical stimulation lead includes a lead body having a distal end portion, a proximal end portion, and a longitudinal length; terminals disposed along the proximal end portion of the lead body; electrodes disposed along the distal end portion of the lead body; and conductors extending along the lead body and electrically coupling the terminals to the electrodes. The lead body includes an intermediate portion disposed between the proximal end portion and the distal end portion. The intermediate portion includes at least one separation element that extends longitudinally along the intermediate portion and the intermediate portion is deployable from an undeployed configuration to a deployed configuration responsive to operation of the at least one separation element.

20 Claims, 14 Drawing Sheets

(51) Int. Cl.
*A61N 1/372* (2006.01)
*A61N 1/08* (2006.01)
*A61N 1/378* (2006.01)
*A61N 1/375* (2006.01)

(52) U.S. Cl.
CPC .......... *A61N 1/0539* (2013.01); *A61N 1/0551* (2013.01); *A61N 1/08* (2013.01); *A61N 1/36114* (2013.01); *A61N 1/378* (2013.01); *A61N 1/37514* (2017.08)

(58) Field of Classification Search
CPC ...... A61N 1/08; A61N 1/378; A61N 1/36114; A61N 1/37514
See application file for complete search history.

(56) References Cited

U.S. PATENT DOCUMENTS

| | | |
|---|---|---|
| 4,744,370 A | 5/1988 | Harris |
| 5,000,194 A | 3/1991 | van den Honert et al. |
| 5,070,605 A | 12/1991 | Daglow et al. |
| 5,135,001 A | 8/1992 | Sinofsky et al. |
| 5,348,481 A | 9/1994 | Ortiz |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,125,302 A | 9/2000 | Kuzma |
| 6,134,478 A | 10/2000 | Spehr |
| 6,161,047 A | 12/2000 | King et al. |
| 6,162,101 A | 12/2000 | Fischer et al. |
| 6,167,311 A | 12/2000 | Rezai |
| 6,181,969 B1 | 1/2001 | Gord |
| 6,322,559 B1 | 11/2001 | Daulton et al. |
| 6,428,336 B1 | 8/2002 | Akerfeldt |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,663,570 B2 | 12/2003 | Mott et al. |
| 6,678,564 B2 | 1/2004 | Ketterl et al. |
| 6,741,892 B1 | 5/2004 | Meadows et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,108,549 B2 | 9/2006 | Lyu et al. |
| 7,203,548 B2 | 4/2007 | Whitehurst et al. |
| 7,241,180 B1 | 7/2007 | Rentas |
| 7,244,150 B1 | 7/2007 | Brase et al. |
| 7,292,890 B2 | 11/2007 | Whitehurst et al. |
| 7,402,083 B2 | 7/2008 | Kast et al. |
| 7,437,193 B2 | 10/2008 | Parramon et al. |
| 7,450,997 B1 | 11/2008 | Pianca et al. |
| 7,489,971 B1 | 2/2009 | Franz |
| 7,668,601 B2 | 2/2010 | Hegland et al. |
| 7,672,734 B2 | 3/2010 | Anderson et al. |
| 7,736,191 B1 | 6/2010 | Sochor |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,074 B2 | 10/2011 | Barker |
| 8,099,177 B2 | 1/2012 | Dahlberg |
| 8,100,726 B2 | 1/2012 | Harlan et al. |
| 8,140,163 B1 | 3/2012 | Daglow et al. |
| 8,175,710 B2 | 5/2012 | He |
| 8,190,259 B1 | 5/2012 | Smith |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,483,237 B2 | 7/2013 | Zimmerman et al. |
| 8,583,237 B2 | 11/2013 | Bedenbaugh |
| 8,688,235 B1 | 4/2014 | Pianca et al. |
| 8,849,415 B2 | 9/2014 | Bedenbaugh |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,270,070 B2 | 2/2016 | Pianca |
| 9,289,596 B2 | 3/2016 | Leven |
| 9,352,147 B2 | 5/2016 | Nguyen-Stella |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,620 B2 | 11/2016 | Romero et al. |
| 9,504,839 B2 | 11/2016 | Leven |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0071320 A1 | 3/2008 | Brase |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |

(56) References Cited

U.S. PATENT DOCUMENTS

| | | |
|---|---|---|
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0259386 A1 | 10/2012 | DeRohan et al. |
| 2012/0316615 A1 | 12/2012 | DiGiore et al. |
| 2013/0105071 A1 | 5/2013 | DiGiore et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0180375 A1 | 6/2014 | Pianca et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0142010 A1* | 5/2015 | Min ............... A61N 1/0551 606/129 |
| 2015/0151113 A1 | 6/2015 | Govea et al. |
| 2015/0360023 A1 | 12/2015 | Howard et al. |
| 2015/0374978 A1 | 12/2015 | Howard et al. |
| 2016/0045723 A1* | 2/2016 | Bornzin ............... A61N 1/0534 607/45 |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0228692 A1 | 8/2016 | Steinke et al. |
| 2016/0296745 A1 | 10/2016 | Govea et al. |
| 2017/0014635 A1 | 1/2017 | Villarta et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

* cited by examiner

FORCE-DECOUPLED AND STRAIN RELIEVING LEAD AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/441,948, filed Jan. 3, 2017, which is incorporated herein by reference.

FIELD

The present invention is directed to the area of implantable electrical stimulation systems and methods of making and using the systems. The present invention is also directed to electrical stimulation leads, systems, and methods of making and using the electrical stimulation leads.

BACKGROUND

Implantable electrical stimulation systems have proven therapeutic in a variety of diseases and disorders. For example, stimulation of the brain, such as deep brain stimulation, can be used to treat a variety of diseases or disorders and spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the brain, nerves, or other tissue to be stimulated. The pulse generator in the control module generates electrical pulses that are delivered by the electrodes to body tissue.

BRIEF SUMMARY

One embodiment is an electrical stimulation lead that includes a lead body having a distal end portion, a proximal end portion, and a longitudinal length; terminals disposed along the proximal end portion of the lead body; electrodes disposed along the distal end portion of the lead body; and conductors extending along the lead body and electrically coupling the terminals to the electrodes. The lead body includes an intermediate portion disposed between the proximal end portion and the distal end portion. The intermediate portion includes at least one separation element that extends longitudinally along the intermediate portion and the intermediate portion is deployable from an undeployed configuration to a deployed configuration responsive to operation of the at least one separation element.

In at least some embodiments, when the intermediate portion is in the deployed configuration, the conductors are arranged in at least one row in the intermediate portion, each of the at least one row including at least two of the conductors, each of the at least one row being linear or arc-shaped when the intermediate portion is in the deployed configuration. In at least some embodiments, the at least one separation element includes at least two separation elements, wherein the intermediate portion further includes at least two sections that are separated from each other by the at least two separation elements, wherein the at least two sections, when the intermediate portion is in the deployed configuration, are spaced apart from each other.

In at least some embodiments, the at least one separation element includes a slider operable by sliding the slider to deploy the intermediate portion from the undeployed configuration to the deployed configuration. In at least some embodiments, the slider includes a blade configured and arranged to separate opposing edges of the intermediate portion when the slider is operated. In at least some embodiments, the slider includes a graspable feature configured and arranged for grasping by a user or tool to operate the slider. In at least some embodiments, the slider includes an aperture for receiving a portion of a tool to operate the slider using the tool.

In at least some embodiments, the at least one separation element is configured and arranged for operation by a stylet inserted into the lead and into the intermediate portion to deploy the intermediate portion from the undeployed configuration to the deployed configuration. In at least some embodiments, the at least one separation element includes at least one material configured and arranged, responsive to application of a chemical reactant, a solvent, or light having a predefined wavelength, to deploy the intermediate portion from the undeployed configuration to the deployed configuration. In at least some embodiments, the at least one separation element includes at least one registration structure configured and arranged, responsive to a mechanical force to separate portions of the registration structure, to deploy the intermediate portion from the undeployed configuration to the deployed configuration.

In at least some embodiments, in the undeployed configuration, the intermediate portion defines a central lumen with the conductors arranged concentrically about the central lumen of the intermediate portion, wherein, in the deployed configuration, the intermediate portion defines at least one row of the conductors, wherein each of the at least one row includes at least two of the conductors, wherein each of the at least one row is linear or arc-shaped when the intermediate portion is in the deployed configuration.

Another embodiment is an electrical stimulation lead that includes a lead body having a distal end portion, a proximal end portion, and a longitudinal length; terminals disposed along the proximal end portion of the lead body; electrodes disposed along the distal end portion of the lead body; and conductors extending along the lead body and electrically coupling the terminals to the electrodes. The lead body includes a cylindrical portion and a non-cylindrical portion, where the cylindrical portion includes the distal end portion and the proximal end portion and the non-cylindrical portion is disposed between the proximal end portion and the distal end portion. In the non-cylindrical portion, the conductors are arranged in at least one row, wherein each of the at least one row includes at least two of the conductors and wherein each of the at least one row is linear or arc-shaped.

In at least some embodiments, the cylindrical portion includes a central lumen in both the proximal end portion and the distal end portion, and the lead is configured and arranged to permit a stylet to extend from the central lumen of the proximal end portion to the central lumen of the distal end portion while the stylet bypasses the non-cylindrical portion.

In at least some embodiments, the cylindrical portion includes a central lumen in both the proximal end portion and the distal end portion, and the non-cylindrical portion includes a stylet lumen that permits a stylet to extend from the central lumen of the proximal end portion, through the stylet lumen of the non-cylindrical portion, to the central lumen of the distal end portion. In at least some embodiments, in the non-cylindrical portion, each of the conductors is disposed in a separate conductor lumen, wherein each of the at least one row includes at least two of the conductor lumens and the stylet lumen is disposed in one of the at least one row. In at least some embodiments, the non-cylindrical portion defines an attachment element includes the stylet lumen and is adjacent to at least one of the at least one row of the conductors.

In at least some embodiments, the cylindrical portion includes a central lumen in both the proximal end portion and the distal end portion, and, in the cylindrical portion, the conductors are disposed concentrically around the central lumen. In at least some embodiments, the cylindrical portion includes a central lumen in both the proximal end portion and the distal end portion, wherein the cylindrical portion further includes a plurality of first conductor lumens disposed concentrically around the central lumen, wherein part of the conductors are disposed in the first conductor lumens, wherein the non-cylindrical portion defines at least one row of second conductor lumens with the conductors extending through the second conductor lumens, wherein each of the at least one row of the second conductor lumens includes at least two of the second conductor lumens, wherein each of the at least one row of the second conductor lumens is linear or arc-shaped, and a number of the second conductor lumens equals a number of the first conductor lumens.

A further embodiment is an electrical stimulation system that includes any of the leads described above; and a control module coupleable to the lead and including a housing and an electronic subassembly disposed in the housing.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to electrical stimulation leads, systems, and methods of making and using the electrical stimulation leads.

Suitable implantable electrical stimulation systems include, but are not limited to, an electrode lead ("lead") with one or more electrodes disposed on a distal end portion of the lead and one or more terminals disposed on one or more proximal end portions of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Figure 1A:
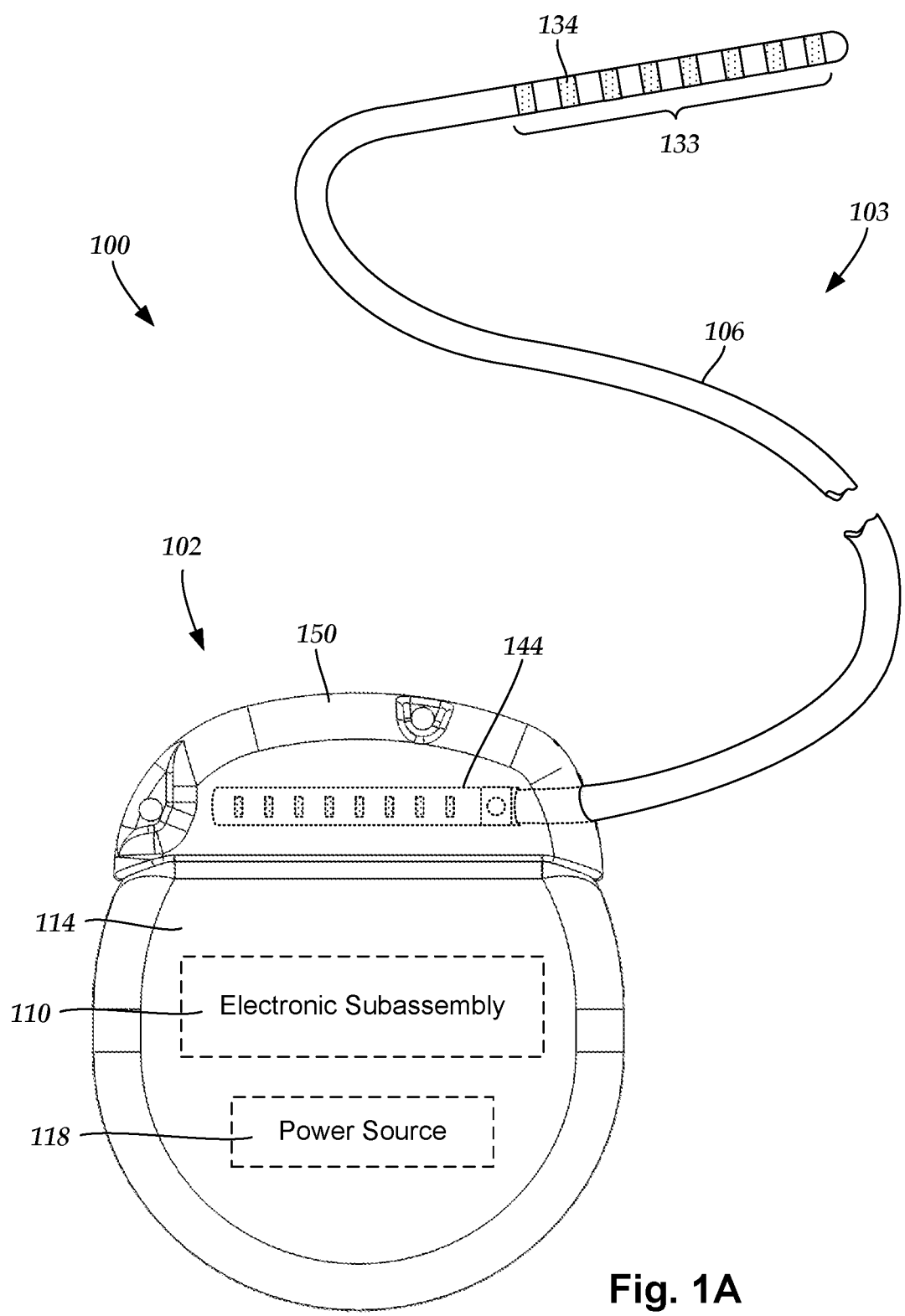
FIG. 1A is a schematic view of some embodiments of an electrical stimulation system that includes a percutaneous lead body coupled to a control module, according to the invention.

FIG. 1A schematically illustrates some embodiments of an electrical stimulation system 100. The electrical stimulation system 100 includes a control module (for example, a stimulator or pulse generator) 102 and a percutaneous lead 103. The lead 103 includes multiple electrodes 134 that form an array of electrodes 133. The control module 102 typically includes an electronic subassembly 110 and an optional power source 118 disposed in a sealed housing 114. The lead 103 includes a lead body 106 coupling the control module 102 to the plurality of electrodes 134. In at least some embodiments, the lead body 106 is isodiametric.

The control module 102 typically includes one or more connector assemblies 144 into which the proximal end portion of the lead body 106 can be plugged to make an electrical connection via connector contacts (for example, 216 in FIG. 2A) disposed in the connector assembly 144 and terminals (for example, 210 in FIG. 2A) disposed along the lead body 106. The connector contacts are coupled to the electronic subassembly 110 and the terminals are coupled to the electrodes 134. Optionally, the control module 102 may include a plurality of connector assemblies 144.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions (not shown) can be disposed between the lead body 106 and the control module 102 to extend the distance between the lead body 106 and the control module 102.

The electrical stimulation system or components of the electrical stimulation system, including the lead body 106 and the control module 102, are typically implanted into the body of a patient. The electrical stimulation system 100 can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of the following materials: platinum, platinum iridium, palladium, or titanium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1A, eight electrodes 134 are shown. The electrodes 134 can be formed in any suitable shape including, for example, round, oval, triangular, rectangular, pentagonal, hexagonal, heptagonal, octagonal, or the like. In the illustrated lead 103, the electrodes 134 are ring electrodes. Any number of ring electrodes can be disposed along the length of the lead body including, for example, one, two three, four, five, six, seven, eight, nine, ten, eleven, twelve, thirteen, fourteen, fifteen, sixteen or more ring electrodes. It will be understood that any number of ring electrodes can be disposed along the length of the lead body 106.

Figure 1B:
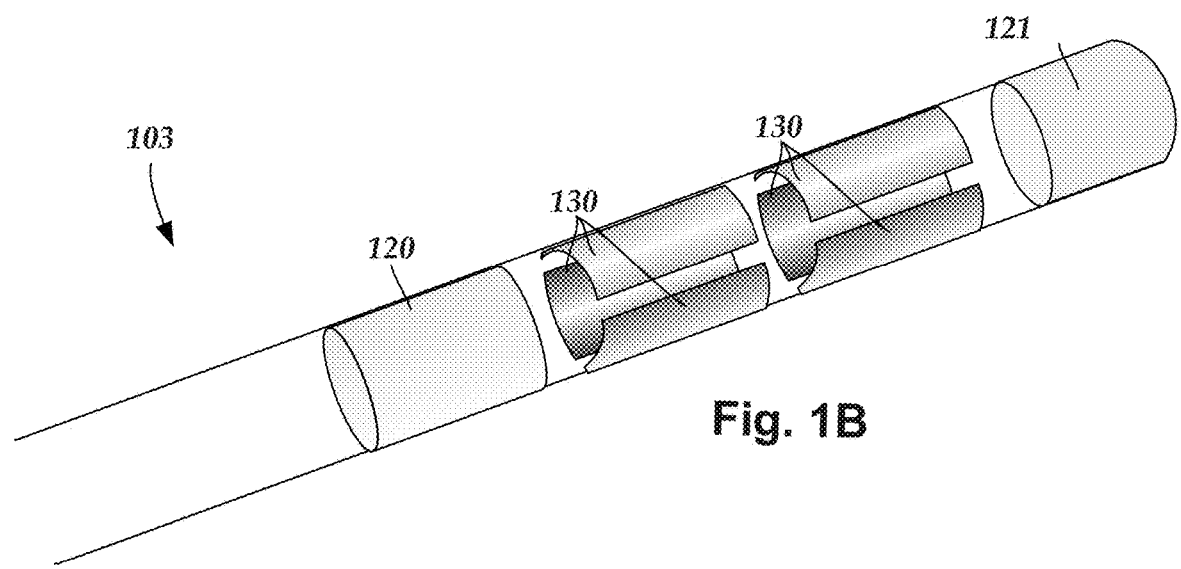
FIG. 1B is a schematic perspective view of some embodiments of a distal portion of the lead body of FIG. 1A, according to the invention.

FIG. 1B schematically illustrates a distal end portion of the lead 103 with a ring electrode 120, a tip electrode 121, and six segmented electrodes 130 in the distal electrode array 133. Segmented electrodes 130 may provide for superior current steering than ring electrodes 120 because target structures may not be disposed symmetrically about a longitudinal axis of the distal electrode array 133. Instead, a target may be located on one side of a plane running through the axis of the lead 103. Through the use of a radially segmented electrode array ("RSEA"), current steering can be performed not only along a length of the lead 103 but also around a circumference of the lead 103. This provides precise three-dimensional targeting and delivery of the current stimulus to target tissue, while potentially avoiding stimulation of other tissue.

Examples of leads with segmented electrodes include U.S. Patent Applications Publication Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. Examples of leads with tip electrodes include at least some of the previously cited references, as well as U.S. Patent Applications Publication Nos. 2014/0296953 and 2014/0343647, all of which are incorporated herein by reference in their entireties. A lead with segmented electrodes may be a directional lead that can provide stimulation in a particular direction using the segmented electrodes.

Any number of segmented electrodes 130 may be disposed on the lead body 106 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 106. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes 130, where each set is disposed around a circumference of the lead 103 at a particular longitudinal portion of the lead 103. The lead 103 may have any number segmented electrodes 130 in a given set of segmented electrodes 130. The lead 103 may have one, two, three, four, five, six, seven, eight, or more segmented electrodes 130 in a given set. The segmented electrodes 130 may vary in size and shape. In at least some embodiments, the segmented electrodes 130 are all of the same size, shape, diameter, width or area or any combination thereof. In at least some embodiments, the segmented electrodes 130 of each circumferential set (or even all segmented electrodes disposed on the lead 103) may be identical in size and shape.

Each set of segmented electrodes 130 may be disposed around the circumference of the lead body 106 to form a substantially cylindrical shape around the lead body 106. The spacing between individual segmented electrodes 130 of a given set of the segmented electrodes 130 may be the same, or different from, the spacing between individual electrodes of another set of segmented electrodes 130 on the lead 103. In at least some embodiments, equal spaces, gaps or cutouts are disposed between each segmented electrode 130 around the circumference of the lead body 106. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 106.

Each electrode 134 in the array of electrodes 133 of the lead body 106 are typically disposed in, or separated by, a non-conductive, biocompatible material including, for example, silicone, polyurethane, polyetheretherketone ("PEEK"), epoxy, perfluoroalkoxy alkane (PFA), and the like or combinations thereof. The lead body 106 may be formed in the desired shape by any process including, for example, extruding, molding (including injection molding), casting, and the like. Electrodes 134 and connecting wires can be disposed onto or within the lead body 106 either prior to or subsequent to a molding or casting process. The non-conductive material typically extends from the distal end portion of the lead body 106 to the proximal end portion of the lead body 106.

Terminals (for example, 210 in FIG. 2A) are typically disposed at the proximal end portion of the lead body 106 for connection to corresponding conductive contacts (for example, 216 in FIG. 2A) in one or more connector assemblies (for example, 144 in FIG. 1A) disposed on, for example, the control module 102 (or to other devices, such as conductive contacts on a lead extension, an operating room cable, a splitter, an adaptor, or the like).

Conductive wires extend from the plurality of terminals (see, for example, 210 in FIG. 2A) to the array of electrodes 133. Typically, each of the plurality of terminals is electrically coupled to at least one electrode 134 of the array of electrodes 133. In at least some embodiments, each of the plurality of terminals is coupled to a single electrode 134 of the array of electrodes 133.

The conductive wires may be embedded in the non-conductive material of the lead or can be disposed in one or more lumens (not shown) extending along the lead. In at least some embodiments, there is an individual lumen for each conductive wire. In other embodiments, two or more conductive wires may extend through a lumen. There may also be one or more lumens (not shown) that open at, or near, the proximal end portion of the lead 103, for example, for inserting a stylet rod to facilitate placement of the lead 103 within a body of a patient. Additionally, there may also be one or more lumens (not shown) that open at, or near, the distal end portion of the lead 103, for example, for infusion of drugs or medication into the site of implantation of the lead 103. The one or more lumens may, optionally, be flushed continually, or on a regular basis, with saline or the like. The one or more lumens can be permanently or removably sealable at the distal end portion.

As discussed above, the lead body 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1A, the lead body 106 includes eight terminals that are shown coupled with eight conductive contacts disposed in the connector assembly 144.

Figure 2A:
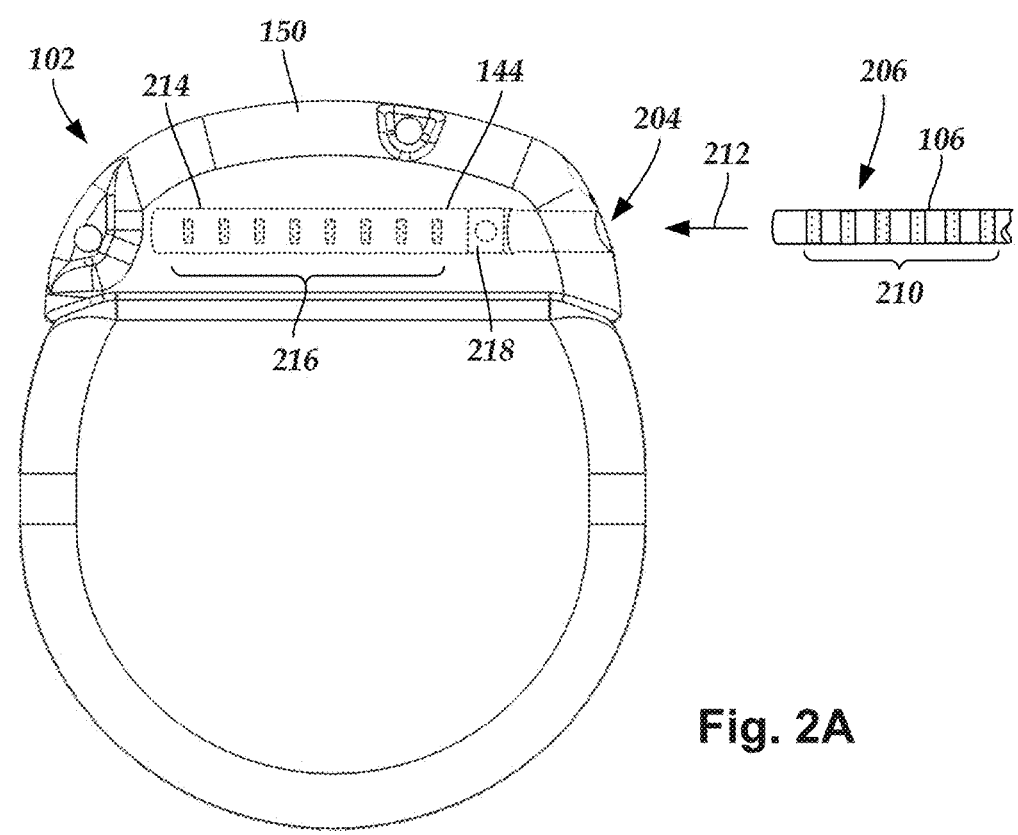
FIG. 2A is a schematic view of some embodiments of a plurality of connector assemblies disposed in the control module of FIG. 1A, the connector assemblies configured and arranged to receive proximal portions of the lead body of FIG. 1A, according to the invention.

FIG. 2A is a schematic view of some embodiments of a plurality of connector assemblies 144 disposed in the control module 102. In FIG. 2A, the proximal end portion 206 of the lead body 106 is shown configured and arranged for insertion to the control module 102.

In FIG. 2A, the connector assembly 144 is disposed in the header 150. In at least some embodiments, the header 150 defines a port 204 into which the proximal end portion 206 of the lead body 106 with terminals 210 can be inserted, as shown by directional arrow 212, in order to gain access to the connector contacts disposed in the connector assembly 144.

The connector assembly 144 includes a connector housing 214 and a plurality of connector contacts 216 disposed therein. Typically, the connector housing 214 defines a port (not shown) that provides access to the plurality of connector contacts 216. In at least some embodiments, the connector assembly 144 further includes a retaining element 218 configured and arranged to fasten the corresponding lead body 106 or lead retention sleeve to the connector assembly 144 when the lead body 106 is inserted into the connector assembly 144 to prevent undesired detachment of the lead body 106 from the connector assembly 144. For example, the retaining element 218 may include an aperture 220 (FIG. 2B) through which a fastener (for example, a set screw, pin, or the like) may be inserted and secured against an inserted lead body 106 or lead retention sleeve.

When the lead body 106 is inserted into the port 204, the connector contacts 216 can be aligned with the terminals 210 disposed on the lead body 106 to electrically couple the control module 102 to the electrodes (134 of FIG. 1A) disposed at the distal end portion of the lead body 106. Examples of connector assemblies in control modules are found in, for example, U.S. Pat. No. 7,244,150 and U.S. Patent Application Publication No. 2008/0071320, which are incorporated by reference.

Figure 2B:
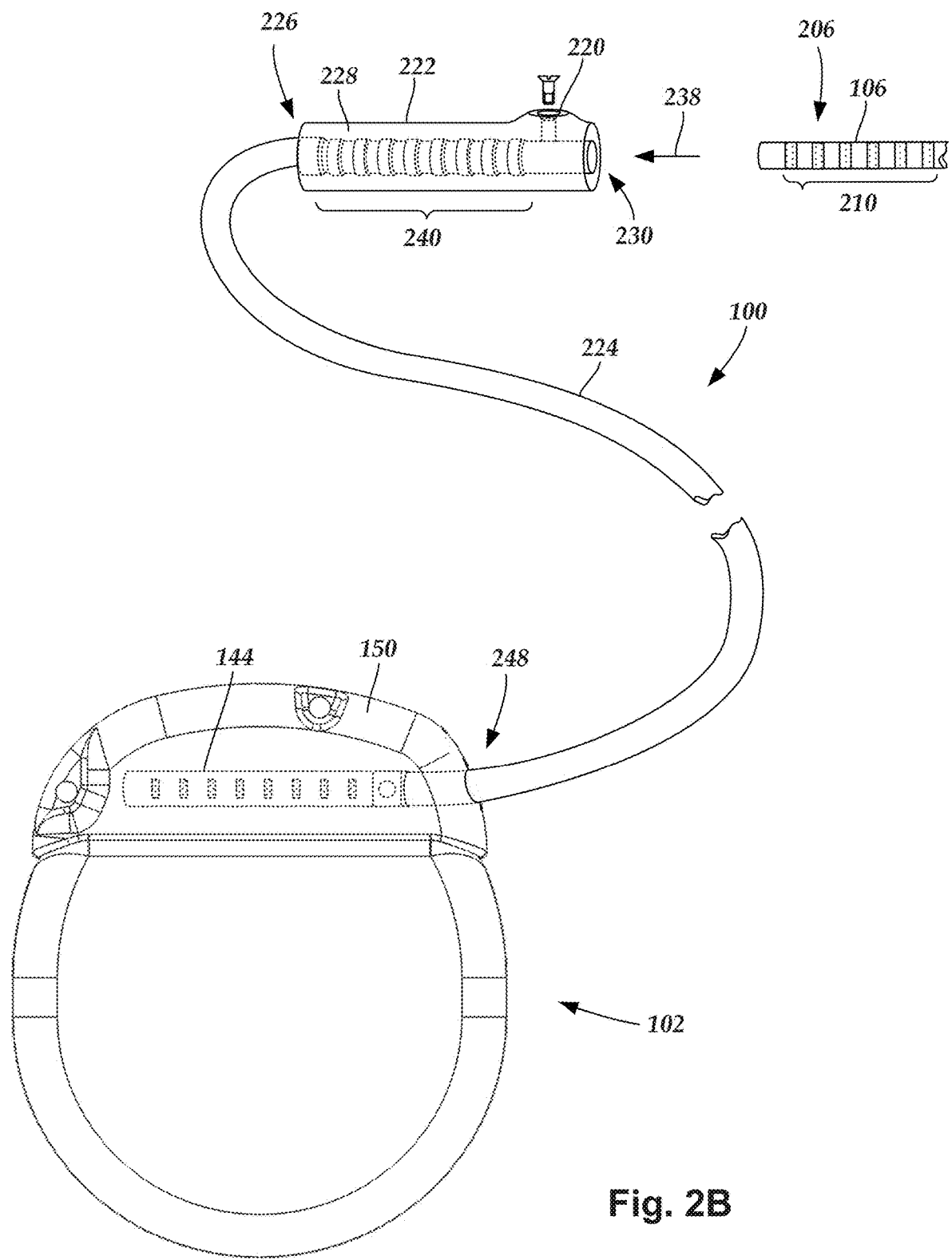
FIG. 2B is a schematic view of some embodiments of a proximal portion of the lead body of FIG. 1A, a lead extension, and the control module of FIG. 1A, the lead extension configured and arranged to couple the lead body to the control module, according to the invention.

In at least some embodiments, the electrical stimulation system 100 includes one or more lead extensions. The lead body 106 can be coupled to one or more lead extensions which, in turn, are coupled to the control module 102. In FIG. 2B, a lead extension connector assembly 222 is disposed on a lead extension 224. The lead extension connector assembly 222 is shown disposed at a distal end portion 226 of the lead extension 224. The lead extension connector assembly 222 includes a contact housing 228. The contact housing 228 defines at least one port 230 into which the proximal end portion 206 of the lead body 106 with terminals 210 can be inserted, as shown by directional arrow 238. The lead extension connector assembly 222 also includes a plurality of connector contacts 240. When the lead body 106 is inserted into the port 230, the connector contacts 240 disposed in the contact housing 228 can be aligned with the terminals 210 on the lead body 106 to electrically couple the lead extension 224 to the electrodes (134 of FIG. 1A) disposed at the distal end portion of the lead body 106.

The proximal end portion of a lead extension can be similarly configured and arranged as a proximal end portion of a lead body. The lead extension 224 may include a plurality of conductive wires (not shown) that electrically couple the connector contacts 240 to terminal on a proximal end portion 248 of the lead extension 224. The conductive wires disposed in the lead extension 224 can be electrically coupled to a plurality of terminals (not shown) disposed on the proximal end portion 248 of the lead extension 224. In at least some embodiments, the proximal end portion 248 of the lead extension 224 is configured and arranged for insertion into a lead extension connector assembly disposed in another lead extension. In other embodiments (as shown in FIG. 2B), the proximal end portion 248 of the lead extension 224 is configured and arranged for insertion into the connector assembly 144 disposed on the control module 102.

Figure 3A:
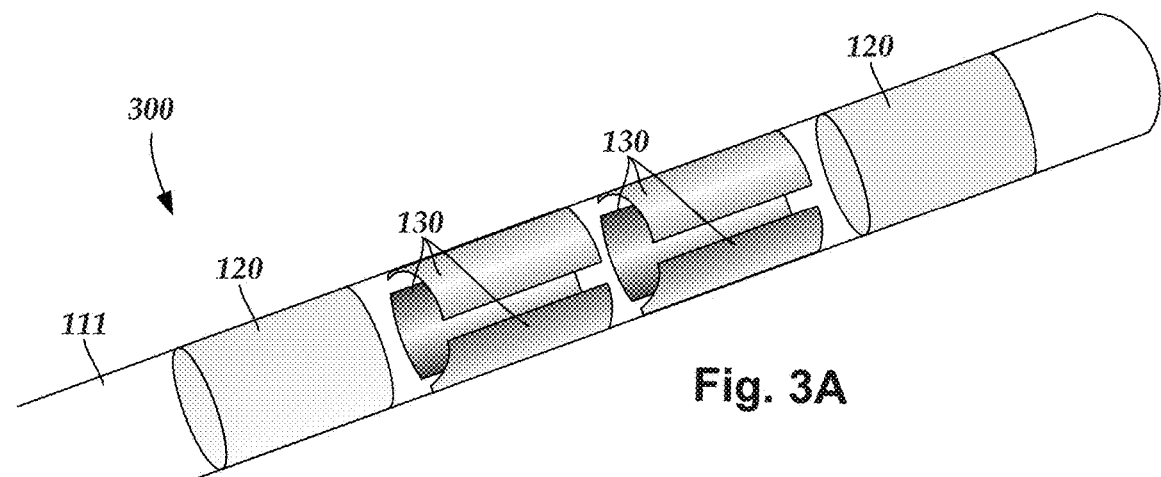
FIG. 3A is a schematic side view of some embodiments of a distal portion of an electrical stimulation lead, according to the invention.
Figure 3B:
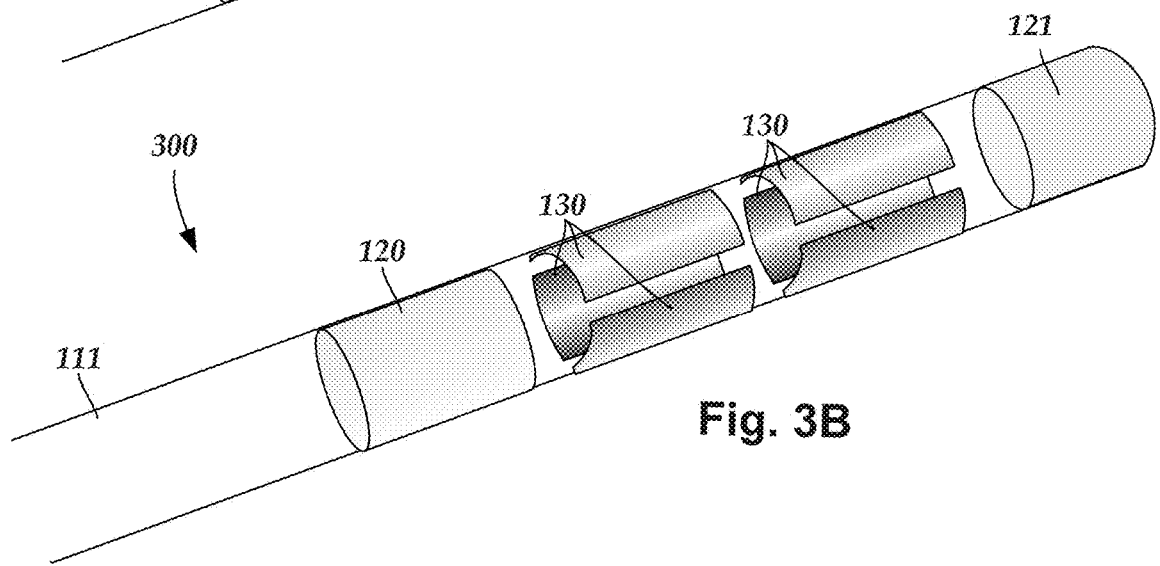
FIG. 3B is a schematic side view of a second embodiment of a distal portion of an electrical stimulation lead, according to the invention.
Figure 3C:
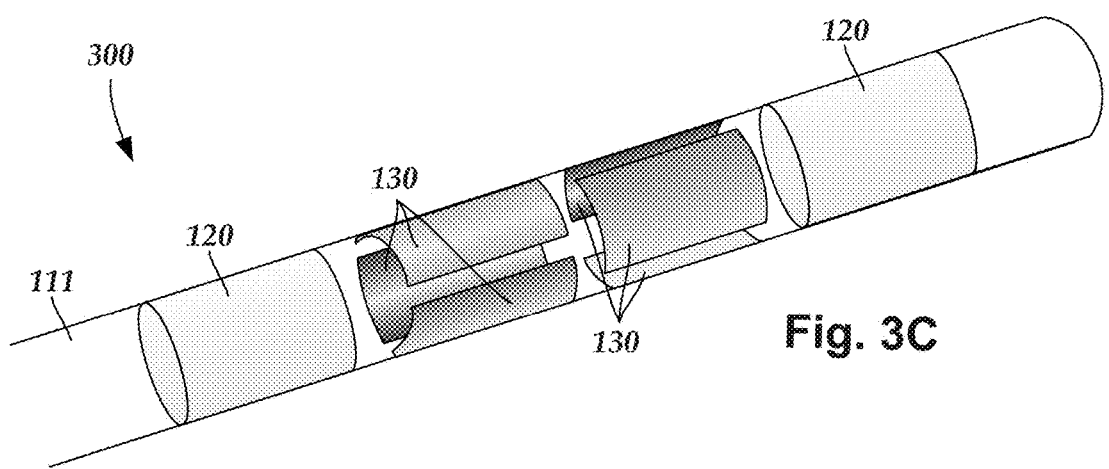
FIG. 3C is a schematic side view of a third embodiment of a distal portion of an electrical stimulation lead, according to the invention.
Figure 3D:
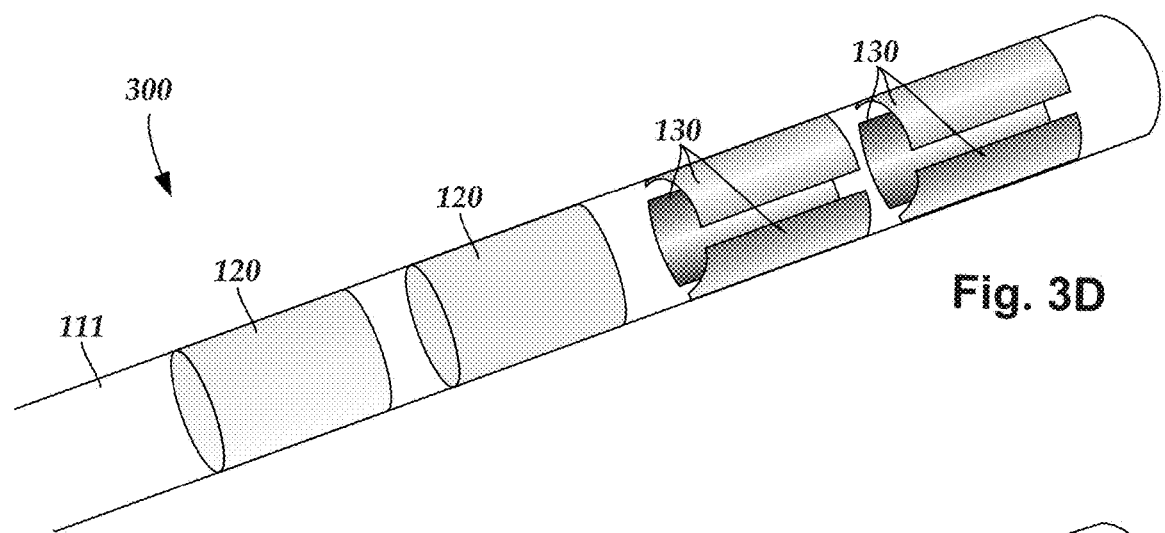
FIG. 3D is a schematic side view of a fourth embodiment of a distal portion of an electrical stimulation lead, according to the invention.
Figure 3E:
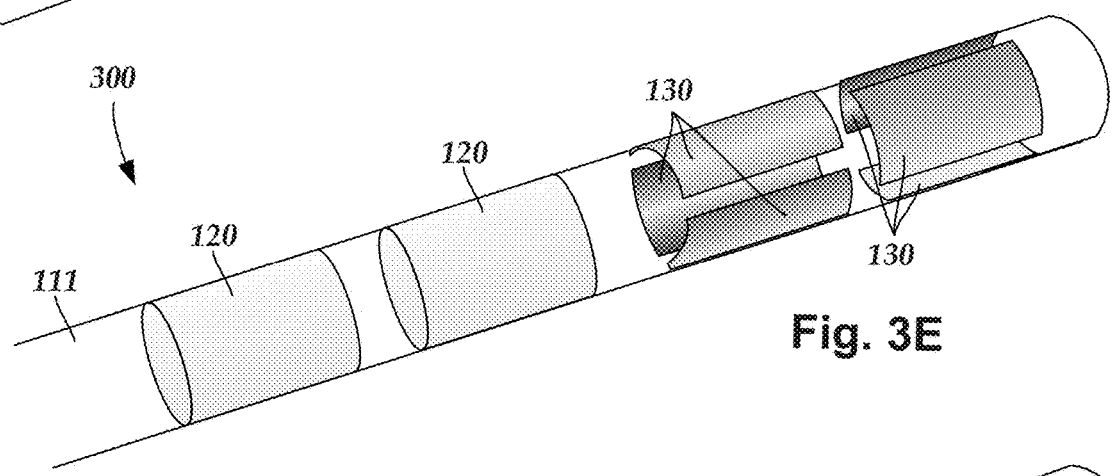
FIG. 3E is a schematic side view of a fifth embodiment of a distal portion of an electrical stimulation lead, according to the invention.
Figure 3F:
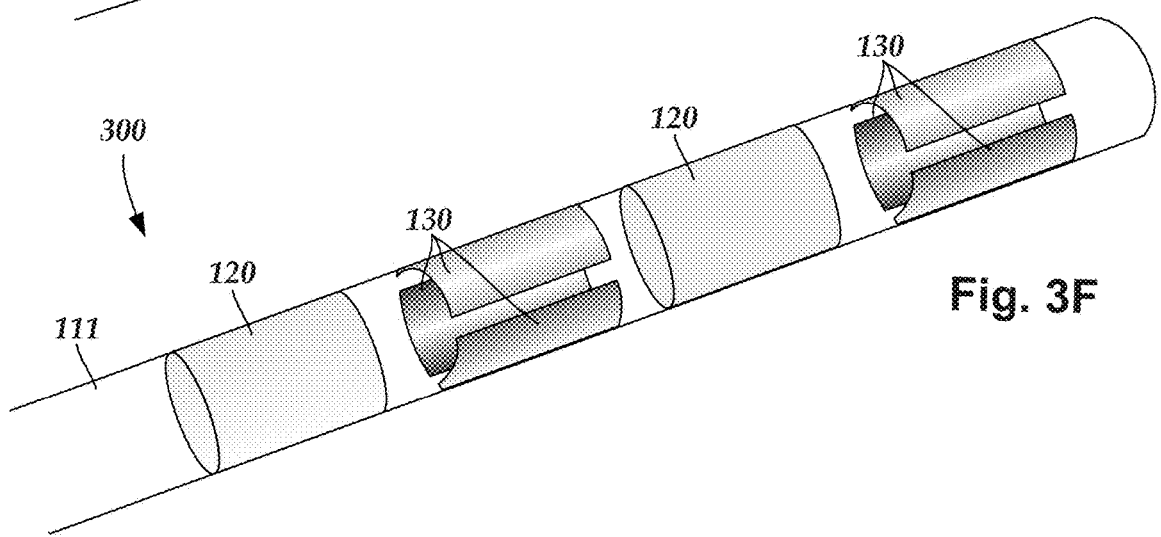
FIG. 3F is a schematic side view of a sixth embodiment of a distal portion of an electrical stimulation lead, according to the invention.
Figure 3G:
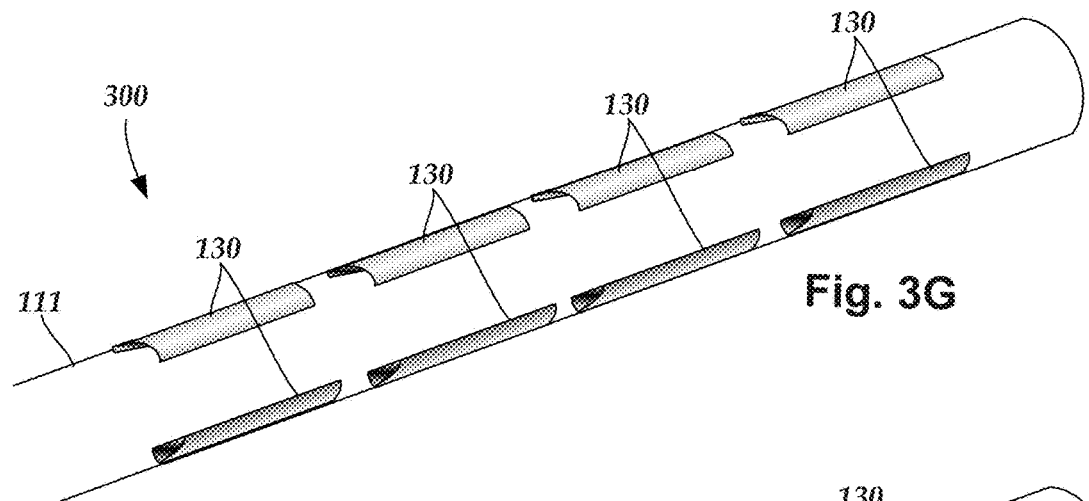
FIG. 3G is a schematic side view of a seventh embodiment of a distal portion of an electrical stimulation lead, according to the invention.
Figure 3H:
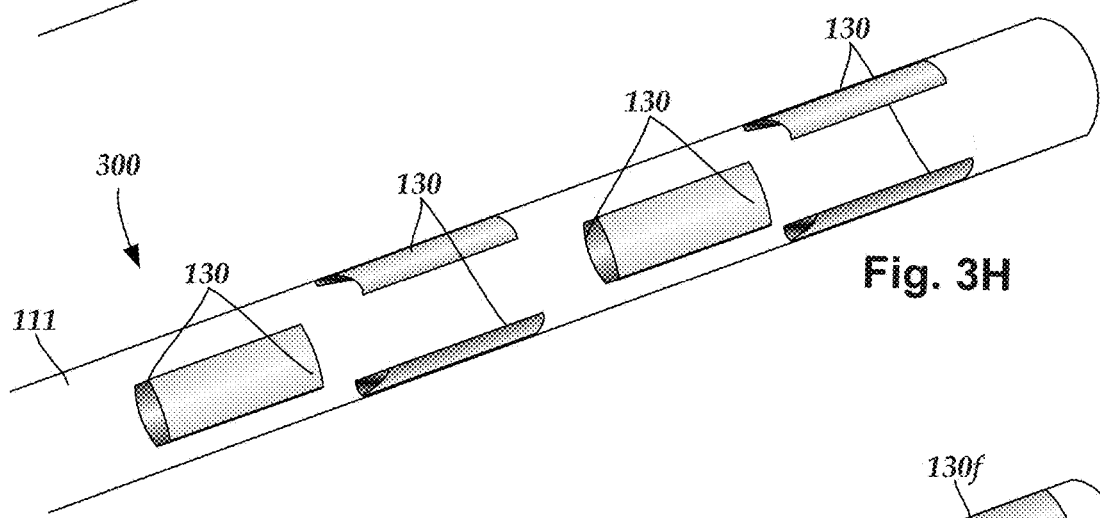
FIG. 3H is a schematic side view of an eighth embodiment of a distal portion of an electrical stimulation lead, according to the invention.

A lead can include ring electrodes, segmented electrodes, tip electrodes, or any other suitable electrode or any combination thereof. A lead containing ring electrodes and segmented electrodes may be arranged in any suitable configuration. FIG. 3A-3I illustrate a variety of different arrangements as non-limiting examples. The arrangements can include ring electrodes 120; segmented electrodes 130, 130a-130h; or tip electrodes 121 disposed along a lead body 111 of a lead 300. In at least some instances, arrangements of electrodes can be written in a shorthand, starting from the distal end portion, with each number indicating the number of electrodes at a particular longitudinal position. For example, the arrangement 1-3-3-1, illustrated in FIG. 3A, indicates a ring electrode 120 at the distal-most position, three segmented electrodes 130 at the next position, another three segmented electrodes 130 at the third position, and a ring electrode 120 at the proximal-most position. In addition, if there are multiple, sequential arrangements of the same type "x" can be used. As an example, the arrangement 3×5–1 (or 3×5+1) indicates five sets of three electrodes spaced apart longitudinally starting from the distal end portion with a single ring electrode 120 at the proximal-most position. Using this notation, the arrangements of the FIGS. 3A-3I can be written as follows: FIG. 3A: 1-3-3-1; FIG. 3B: 1-3-3-1; FIG. 3C: 1-3-3-1; FIG. 3D: 3-3-1-1; FIG. 3E: 3-3-1-1; FIG. 3F: 3-1-3-1; FIG. 3G: 2×4 (or 2-2-2-2); FIG. 3H: 2×4 (or 2-2-2-2); and FIG. 3I: 3×4–2×2 (or 3-3-3-3-2-2).

As non-limiting illustrations of electrode arrangements, when the lead 300 includes two ring electrodes 120 and two sets of segmented electrodes 130, the ring electrodes 120 can flank the two sets of segmented electrodes 130 (see, for example, FIGS. 1B, 3A, 3C). Alternately, the two ring electrodes 120 can be disposed proximal to the two sets of segmented electrodes 130 (see, for example, FIGS. 3D and 3E), or the two ring electrodes 120 can be disposed distal to the two sets of segmented electrodes 130 (not shown) or the two ring electrodes 120 and two sets of segmented electrodes 130 can alternate (see, for example, FIG. 3F). An arrangement may also include a tip electrode 121 (see, for example, FIG. 3B) or a single ring electrode 120 either proximal to, distal to, or between the segmented electrodes (not shown). In arrangements with more than two sets of segmented electrodes 130, the segmented electrodes 130 of the sets may be aligned (see, for example, FIGS. 3A, 3B, 3D, 3F, 3G, and 3I) or staggered (see, for example, FIGS. 3C, 3E, and 3H) relative to each other or in any other suitable relative arrangement. By varying the location of the segmented electrodes 130, different coverage of the target neurons may be selected. For example, the electrode arrangements of FIG. 3D or 3E may be useful if the physician anticipates that the neural target will be closer to a distal tip of the lead body 111. Any combination of ring electrodes 120, tip electrode 121, and segmented electrodes 130 may be disposed on the lead 300.

Figure 3I:
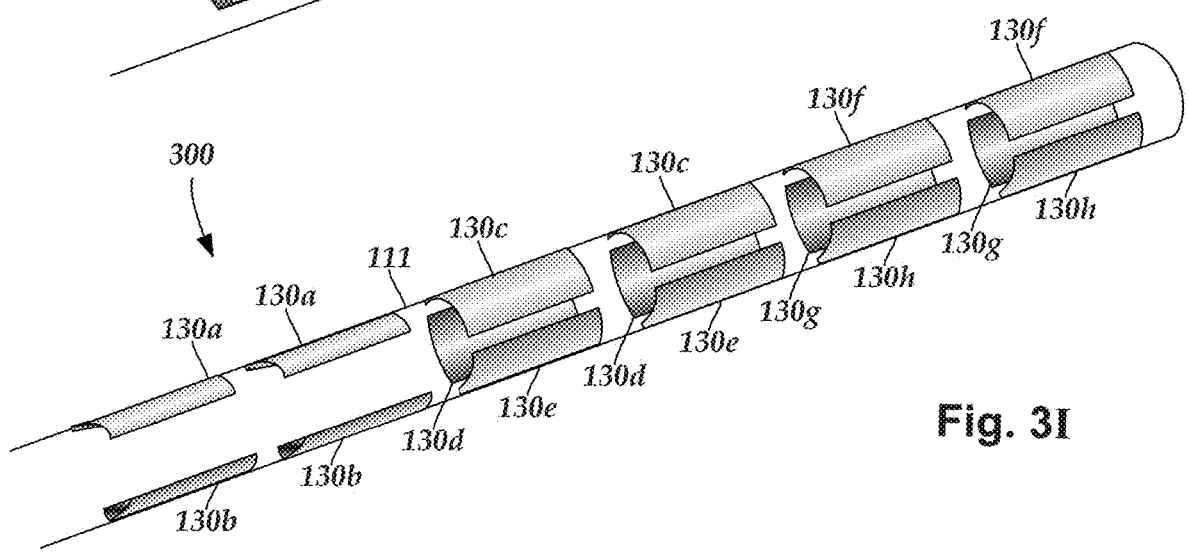
FIG. 3I is a schematic side view of a ninth embodiment of a distal portion of an electrical stimulation lead, according to the invention.

In at least some embodiments, the lead 300 may only include segmented electrodes 130. For example, FIGS. 3G and 3H illustrate the lead 300 with four pairs of segmented electrodes 130 (for example, a 2×4 arrangement) in aligned (FIG. 3G) or staggered configurations (FIG. 3H). Another arrangement has eight pairs of segmented electrodes 130 (for example, a 2×8 arrangement—not shown) in aligned or staggered configuration. FIG. 3I illustrates an arrangement in which different types of sets of segmented electrodes 130a-130h includes—in this case—four sets of three segmented electrodes 130c-130h and two pairs of segmented electrodes 130a, 130b (a 3×4–2×2 arrangement). Another example of a lead with segmented electrodes has the arrangement 3-3-2-3-2-3.

One variation of the arrangement of the lead 300 of FIG. 3I is to electrically gang (i.e., electrically short) segmented electrodes 130a-130h having the same reference numbers (for example, electrically gang the two segmented electrodes labeled 130a, etc.) Such electrical ganging can be accomplished in any suitable manner including by a conductor attached to two electrodes within the lead 100 or be electrically coupling the two electrodes to the same channel in the control module. Two, three, or more electrodes can be ganged together. The ganged electrodes provide longer virtual electrodes. In at least some embodiments, the ganged electrodes have an advantage, over very long individual contacts, of maintaining array flexibility while creating a longer virtual electrode. The ganged configuration maintains directionality and array span. Any other arrangement, including any of the arrangements illustrated in FIGS. 3A-3H, can include two or more sets of electrically ganged electrodes. In at least some embodiments, a lead can include electrodes that are electrically ganged and other electrodes that are not ganged together.

In at least some embodiments, one or more electrodes include surface features to increase surface area of the electrodes. Examples of such surface features include dimples, scores, cuts, trenches, grooves, channels, knurls, or other depressions or roughening of the surface.

Figure 4A:
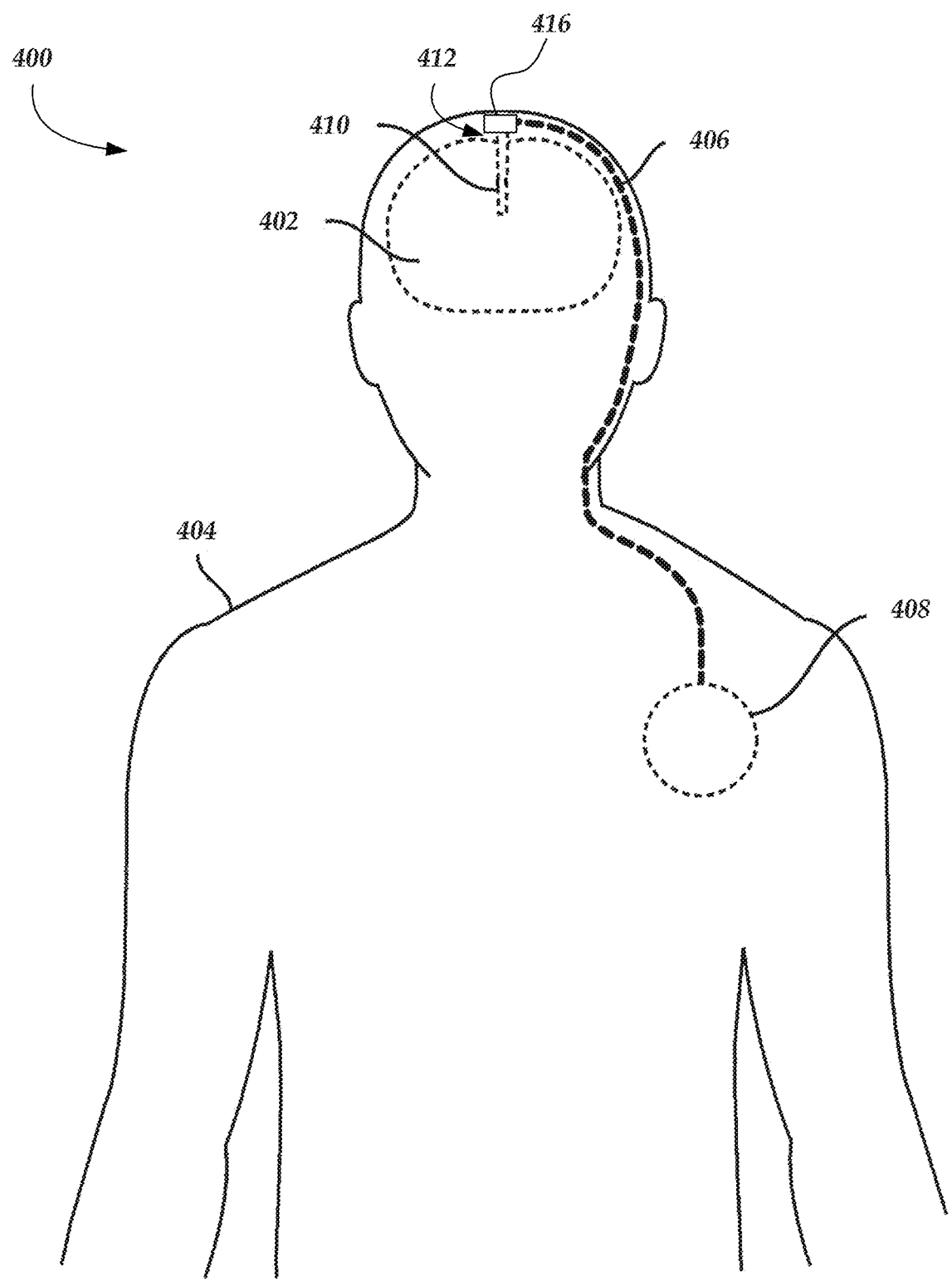
FIG. 4A is a schematic view of one embodiment of an electrical stimulation system with a lead implanted in the brain of a patient, according to the invention.

FIG. 4A illustrates one example of an electrical stimulation system 400 for deep brain stimulation of the brain 402 of a patient 404. The electrical stimulation system includes a lead 406 and a control module 408. It will be understood that the lead 406 and other system components can be implanted elsewhere to achieve other types of stimulation including, but not limited to, spinal cord stimulation or stimulation of other body organs.

A portion of the lead 406 is implanted at the stimulation site and extends through a burr hole in the skull of the patient 404. A burr hole plug 416 is placed on or within the skull 418 (FIG. 4B) around the burr hole and the lead 406 passes through the burr hole plug 416. The control module 408 is typically implanted elsewhere in the body, such as in the torso of the patient 404 or in a subcutaneous pocket. In at least some embodiments, a tunnel (for example, a subcutaneous tunnel) can be formed between the implantation sites of the lead and control module using a tunneling tool, over which a tunneling sheath is disposed. After forming the tunnel, the tunneling tool can be removed leaving the tunneling sheath, and a portion of the lead or a lead extension is slidingly inserted into and through the tunneling sheath.

Figure 4B:
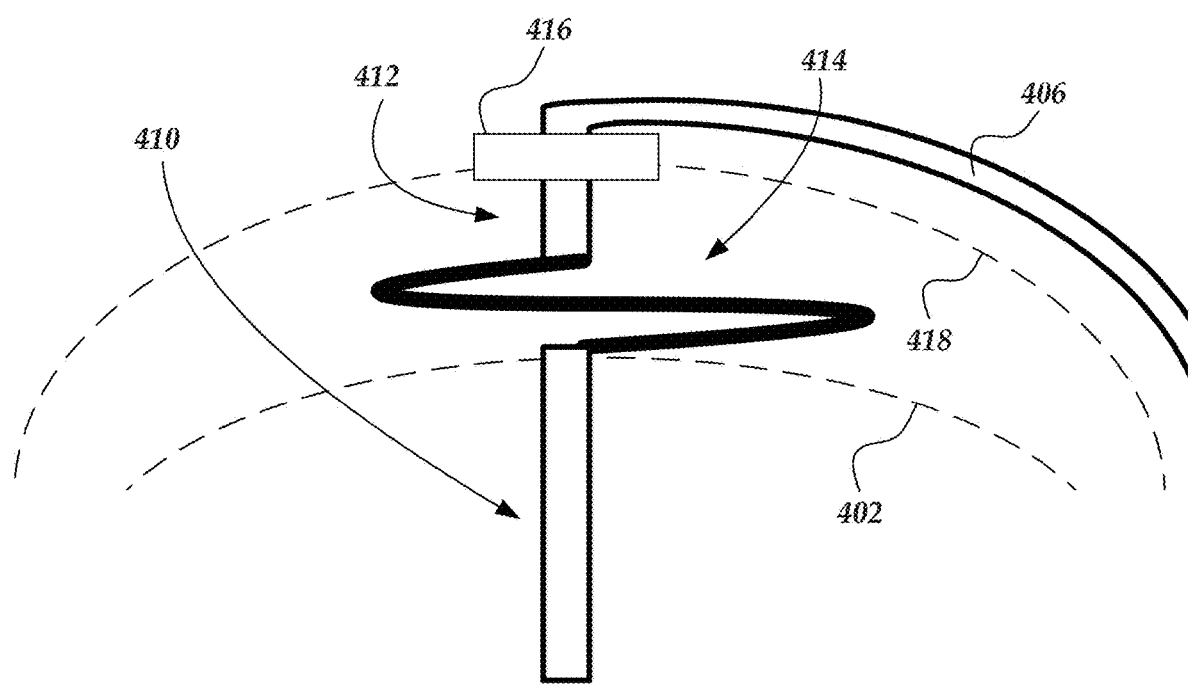
FIG. 4B is a schematic view of one embodiment of the electrical stimulation system of FIG. 4A, including a lead body that comprises an extension portion, an intermediate portion, and a distal end portion, according to the invention.

As illustrated in FIG. 4B, the body of the lead 406 includes a distal end portion 410, an extension portion 412 which extends from an anchoring (or other) location such as the burr hole plug 416 that extends through the skull 418, and an intermediate portion 414 between the distal end portion 410 and the extension portion 412. As shown in the illustrated embodiment, the intermediate portion 414 extends from the distal end portion 410 to the extension portion 412 that has been inserted beyond the bore hole. In at least some embodiments, the intermediate portion 414 may have a length of at least 0.5, 1, 1.5, 2, 2.5, 3, 3.5, 4, 4.5, 5, 6, 7, 8, 9, or 10 centimeters. Typically, the distal end portion 410 bears multiple stimulation electrodes, as described above. In at least some embodiments, the intermediate portion 414 may be defined by that portion of the body of the lead 406 that extends from an anchoring location such as the burr hole plug 416 to the distal electrode array 133 (for example, the extension portion 412 may be omitted in at least some embodiments).

In at least some embodiments, a lead may be anchored at the skull of a patient (for example, at a bore or burr hole), thereby preventing force applied to the part of the lead that is outside the skull from propagating to the part of the lead that is inside the skull (alternatively, the lead may be locked to another bone or structure, instead of the skull). In some cases, however, the target tissue in which a distal end portion of the lead is implanted may move relative to the anchor or lock location (for example, the brain may move relative to the skull). This movement of the target tissue may change the position of the distal end portion of the locked lead relative to the target tissue. In at least some embodiments, to reduce the likelihood of such movement, the intermediate portion 414 is constructed to provide at least some degree of decoupling between the extension and distal portions 410, 412 so that displacement or force on the distal end portion 410 will have no or reduced effect on the extension portion 412 compared to a lead without the intermediate portion 414. For example, the intermediate portion 414 may be more flexible than both the distal end portion 410 of the lead 406 and the extension portion 412 of the lead 406. In at least some embodiments, a greater length of the body of the lead 406 may be inserted into the skull, at least in comparison to a lead that does not include the intermediate portion 414, thereby force-decoupling the distal end portion 410 from the extension portion 412 and providing strain relief due to, for example, movement of the target tissue relative to the extension portion 412. For at least these reasons, the intermediate portion 414 may, in at least some embodiments, increase the likelihood that the distal end portion 410 remains in, for example, an intended location, position, and orientation relative to a target, at least in comparison to a lead that does not include the intermediate portion 414.

Figure 4C:
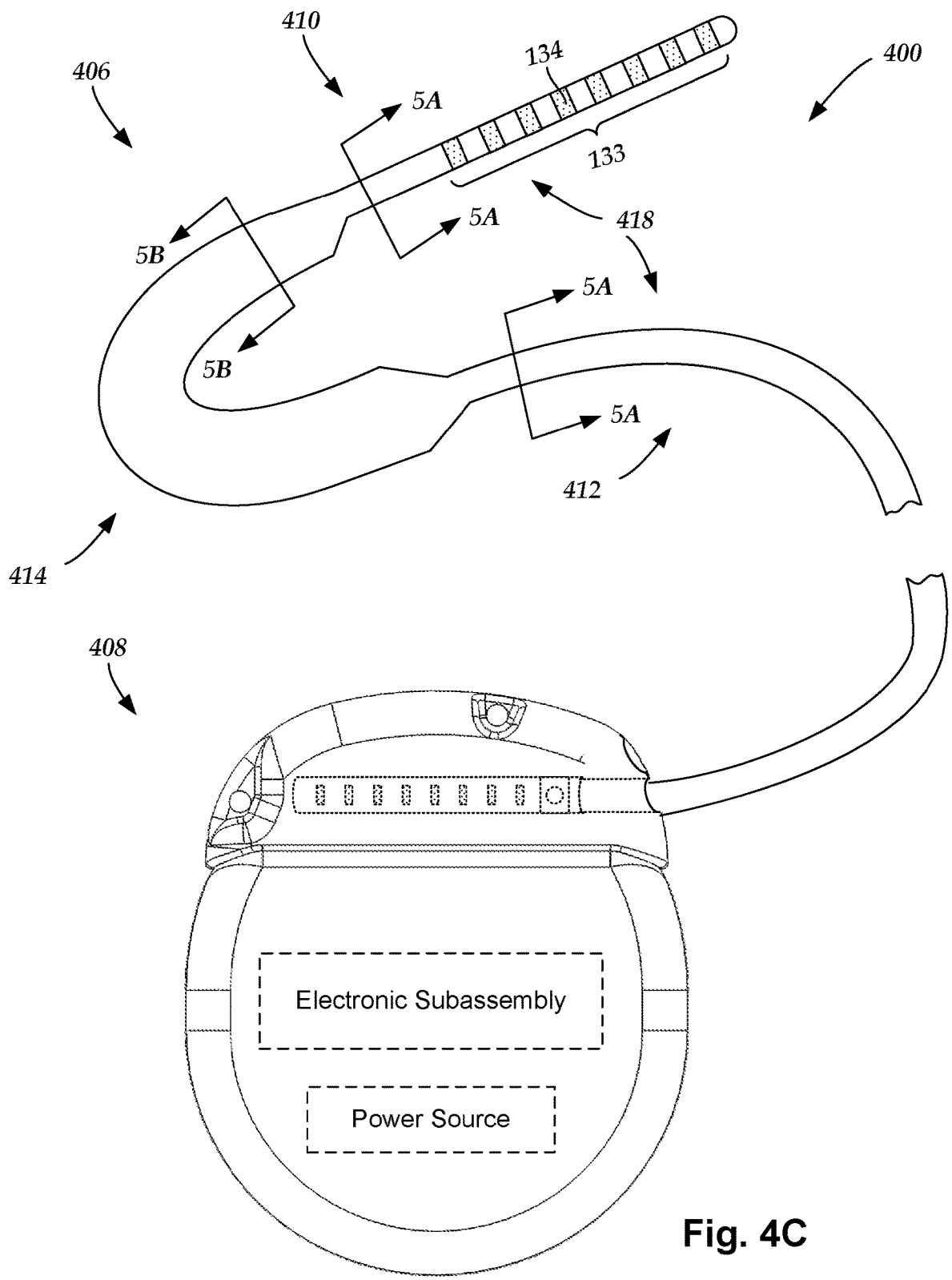
FIG. 4C is a schematic view of one embodiment of the electrical stimulation system of FIG. 4B, including a lead body that comprises a cylindrical portion and a non-cylindrical portion, according to the invention.

FIG. 4C schematically illustrates one embodiment of the electrical stimulation system 400 of FIG. 4B. As with each of the figures, the relative dimensions of the illustrated embodiment are provided for ease of illustration and discussion and do not necessarily correspond to the actual dimensions of a lead. The intermediate portion 414 of the lead body extends from the distal end portion 410 to the extension portion 412. In the illustrated embodiment of FIG. 4C, the lead body is cylindrical along the distal end portion 410 and the extension portion 412, as well as proximal to the extension portion. The intermediate portion 414 is shaped differently and may be, for example, non-cylindrical such as flat or planar or may have another shape such as, but not limited to, an elliptical or arc shape (for example, an arc of up to 15°, 30°, 45°, 60°, 75°, 90°, 105°, 120°, 135°, 150°, 165°, 180°, or more degrees). In at least some embodiments, the intermediate portion 414 may have different shapes at different positions along a longitudinal dimension of the intermediate portion 414. For example, the intermediate portion 414 may have an arc shape at the distal and proximal end portions of the intermediate portion 414 and may be flat or nearly flat between the distal and proximal end portions of the intermediate portion 414.

Figure 5A:
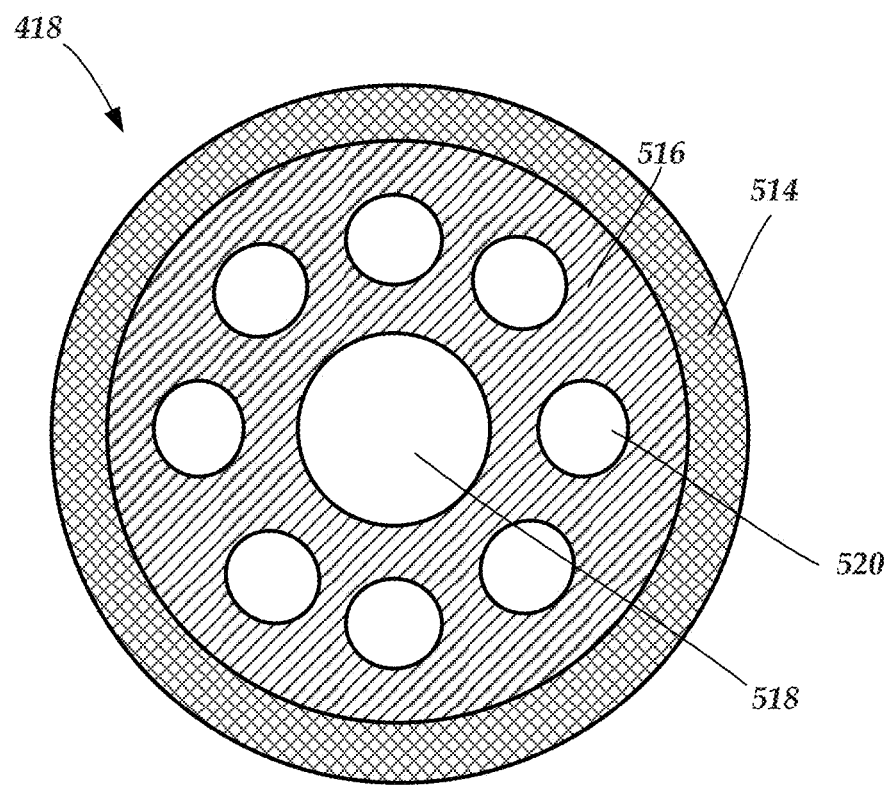
FIG. 5A is a cross-sectional view of one embodiment of at least one part of the cylindrical portion of the lead body of FIG. 4C taken along line 5A-5A of FIG. 4C, according to the invention.

FIG. 5A schematically illustrates a cross-sectional view of one embodiment of the cylindrical portions 418 of the lead body of FIG. 4C taken along lines 5A-5A of FIG. 4C. In the illustrated embodiment, the lead body includes a jacket 514 and a multi-lumen conductor guide 516 (which is disposed within the lead body) that defines a central lumen 518 and multiple conductor lumens 520 which, in the illustrated embodiment, are formed concentrically around the central lumen, as illustrated in FIG. 5A. In the illustrated embodiment, the conductor lumens 520 define tubes within which at least part of the conductors are disposed. In at least some embodiments, at least one of the conductor lumens 520 may simply be the space occupied by a conductor, with or without the conductor's insulator, and is not necessarily separate from or larger than the conductor. The central lumen 506 defines a channel that permits a stylet to extend from inside the channel in the extension portion 412 to inside the channel in the distal end portion 410. In at least some embodiments, the multi-lumen conductor guide 516 is formed as a single piece construction, as illustrated in FIG. 5A. In at least some embodiments, the jacket 514 and the multi-lumen conductor guide 516 are non-conductive, biocompatible, and made from materials such as, for example, silicone, polyurethane, polyetheretherketone ("PEEK"), epoxy, perfluoroalkoxy alkane (PFA), and the like or combinations thereof. In the illustrated embodiment, the cylindrical portions 418 of the lead body have circular cross-sections. In at least some embodiments, the cylindrical portions 418 of the lead body may have octagonal, hexagonal, other regular polygonal, other irregular polygonal, oval, or other tubular cross-sections.

Figure 5E:
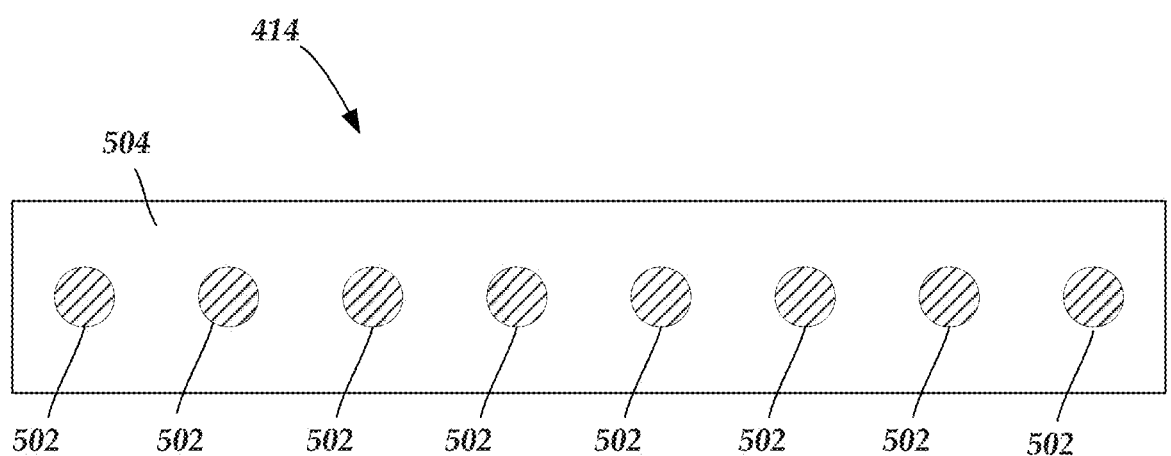
FIG. 5E is a cross-sectional view of another embodiment of the non-cylindrical portion of the lead body of FIG. 4C, according to the invention.
Figure 5B:
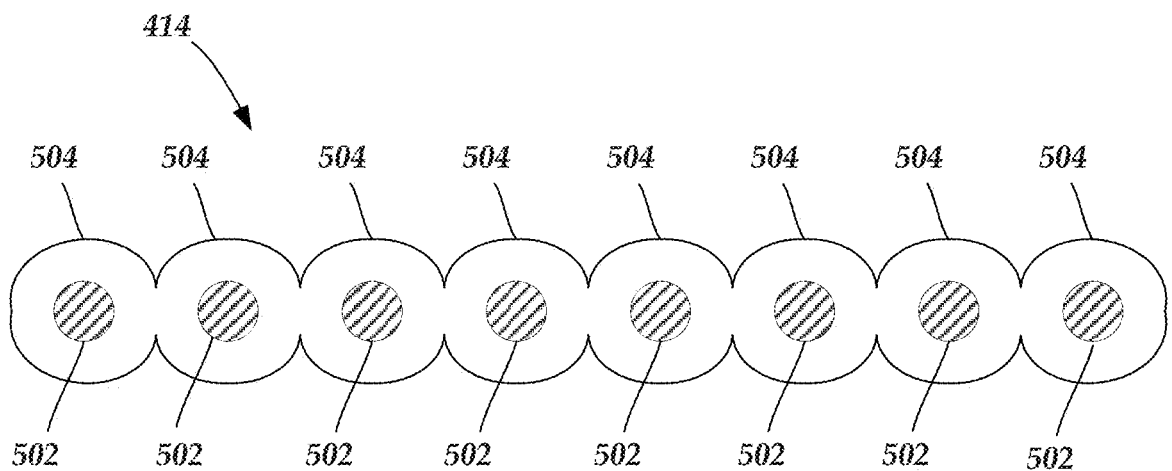
FIG. 5B is a cross-sectional view of one embodiment of the non-cylindrical portion of the lead body of FIG. 4C taken along line 5B-5B of FIG. 4C, according to the invention.

FIG. 5B schematically illustrates a cross-sectional view of one embodiment of the intermediate portion 414 of the lead body of FIG. 4C taken along line 5B-5B of FIG. 4C. In the illustrated embodiment, the intermediate portion 414 has multiple conductors 502 disposed in a non-conductive, biocompatible insulating body 504 made from a material such as, for example, silicone, polyurethane, polyetheretherketone ("PEEK"), epoxy, perfluoroalkoxy alkane (PFA), and the like or combinations thereof. In at least some embodiments, the conductors 502, or conductor lumens, of the intermediate portion 414 are linearly arranged or arranged in an arc-shape. In at least some embodiments, the intermediate portion 414 may define at least one, two, or three linear or arc-shaped rows of conductors 502 or conductor lumens.

Figure 5C:
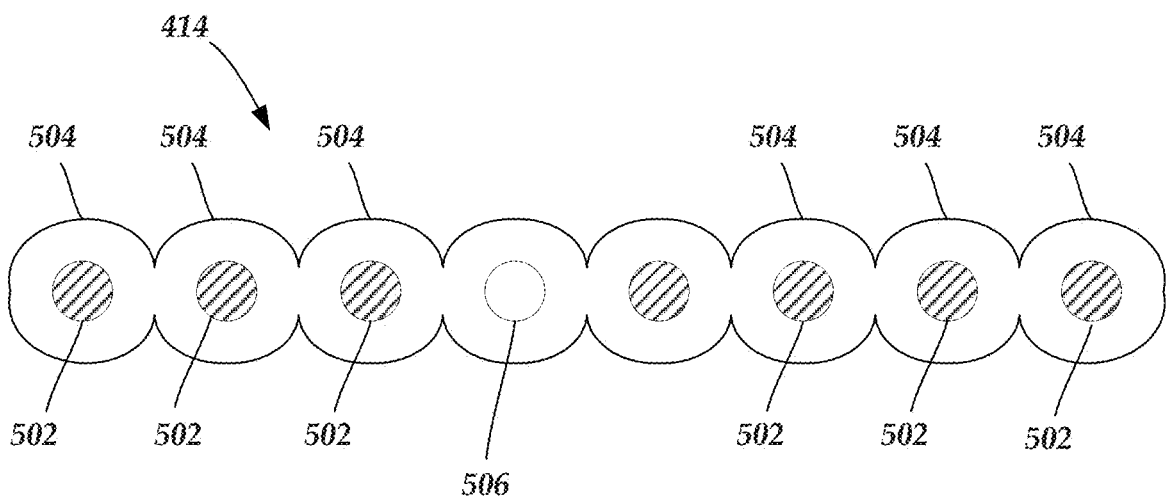
FIG. 5C is a cross-sectional view of another embodiment of the non-cylindrical portion of the lead body of FIG. 4C having an interior lumen, according to the invention.

FIG. 5C schematically illustrates a cross-sectional view of another embodiment of the intermediate portion 414 of the lead body of FIG. 4C taken along line 5B-5B of FIG. 4C. In the illustrated embodiment of FIG. 5C, the intermediate portion 414 includes an interior lumen 506 within the insulating body 504 of the intermediate portion 414. The interior lumen 506 defines a channel that permits a stylet to extend from the central lumen of the extension portion 412, through the intermediate portion 414, to the central lumen of the distal end portion 410.

Figure 5D:
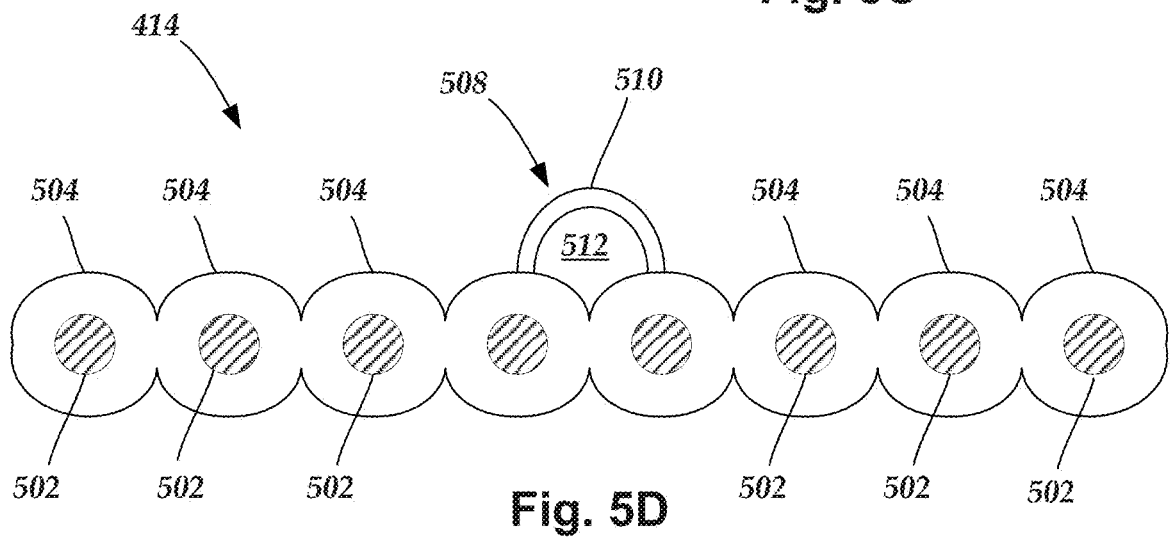
FIG. 5D is a cross-sectional view of a further embodiment of the non-cylindrical portion of the lead body of FIG. 4C having an exterior lumen or attachment element, according to the invention.

FIG. 5D schematically illustrates a cross-sectional view of another embodiment of the intermediate portion 414 of the lead body of FIG. 4C taken along line 5B-5B of FIG. 4C. In the illustrated embodiment of FIG. 5D, the intermediate portion 414 includes an exterior lumen or attachment element 508 that is attached to or formed from the insulating body 504 of the intermediate portion 414. For example, the exterior lumen or attachment element 508 may have a comparative length that is equal to or less than 100, 90, 80, 70, 60, 50, 40, 30, 20, 10, or 5 percent of a total length of the lead 406. By way of example, the exterior lumen or attachment element 508 may take the form of an eyelet member 510 that defines a channel 512 that permits a stylet to extend from the extension portion 412, through the intermediate portion 414, to the distal end portion 410.

FIG. 5E schematically illustrates a cross-sectional view of another embodiment of the intermediate portion 414 of the lead body of FIG. 4C taken along line 5B-5B of FIG. 4C. In the illustrated embodiment of FIG. 5E, the intermediate portion 414 has a single non-conductive, biocompatible insulating body 504. In at least some embodiments, the insulating body 504 may correspond to the multi-lumen conductor guide 516, with or without the jacket 514, of FIG. 5A. While FIG. 5E illustrates the insulating body as a rectangle, the insulating body 414 may have a trapezoidal or any other suitable shape.

In at least some embodiments, the intermediate portion 414 may always be in a non-cylindrical configuration (for example, as illustrated in FIG. 4C). In at least some embodiments, when a stylet is inserted into the lead 406, the stylet can extend from inside the central lumen of the extension portion 412 to inside the central lumen of the distal end portion 410 while bypassing the intermediate portion 414 (or, alternatively, while extending through the intermediate portion 414 via a channel defined by, for example, the interior lumen 506 of FIG. 5C or the aperture 512 of FIG. 5D).

In other embodiments, the intermediate portion 414 is deployable from a cylindrical configuration to a deployed, non-cylindrical configuration (for example, the non-cylindrical configuration illustrated in FIG. 4C). In at least some embodiments, prior to deploying the intermediate portion 414 to the deployed configuration, the intermediate portion 414 may have a cross-section that is the same as or similar to that of the cylindrical portion 418.

Figure 6A:
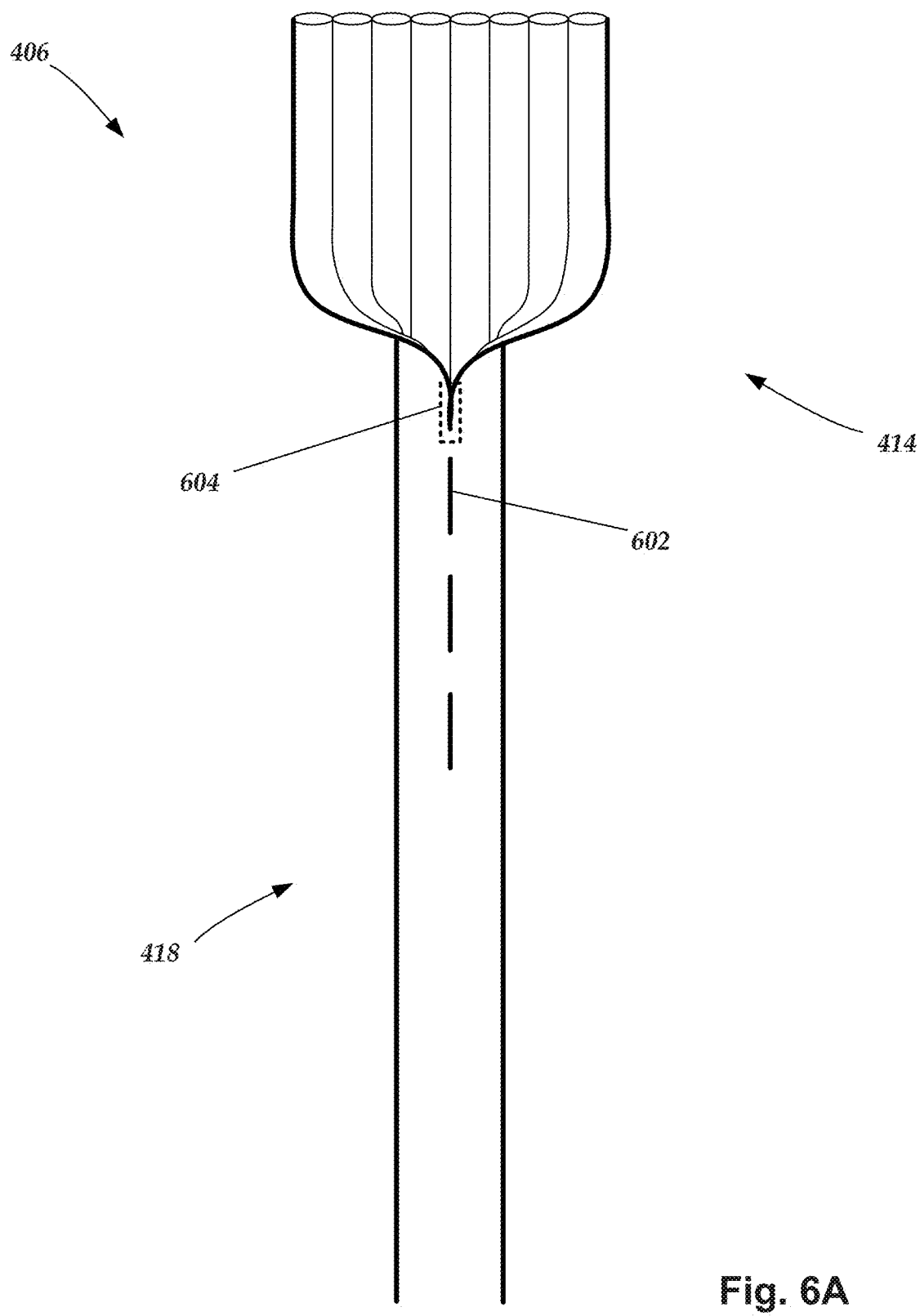
FIG. 6A is a schematic view of one embodiment of part of the cylindrical portion and part of the non-cylindrical portion of the lead body of FIG. 4C, according to the invention.
Figure 6B:
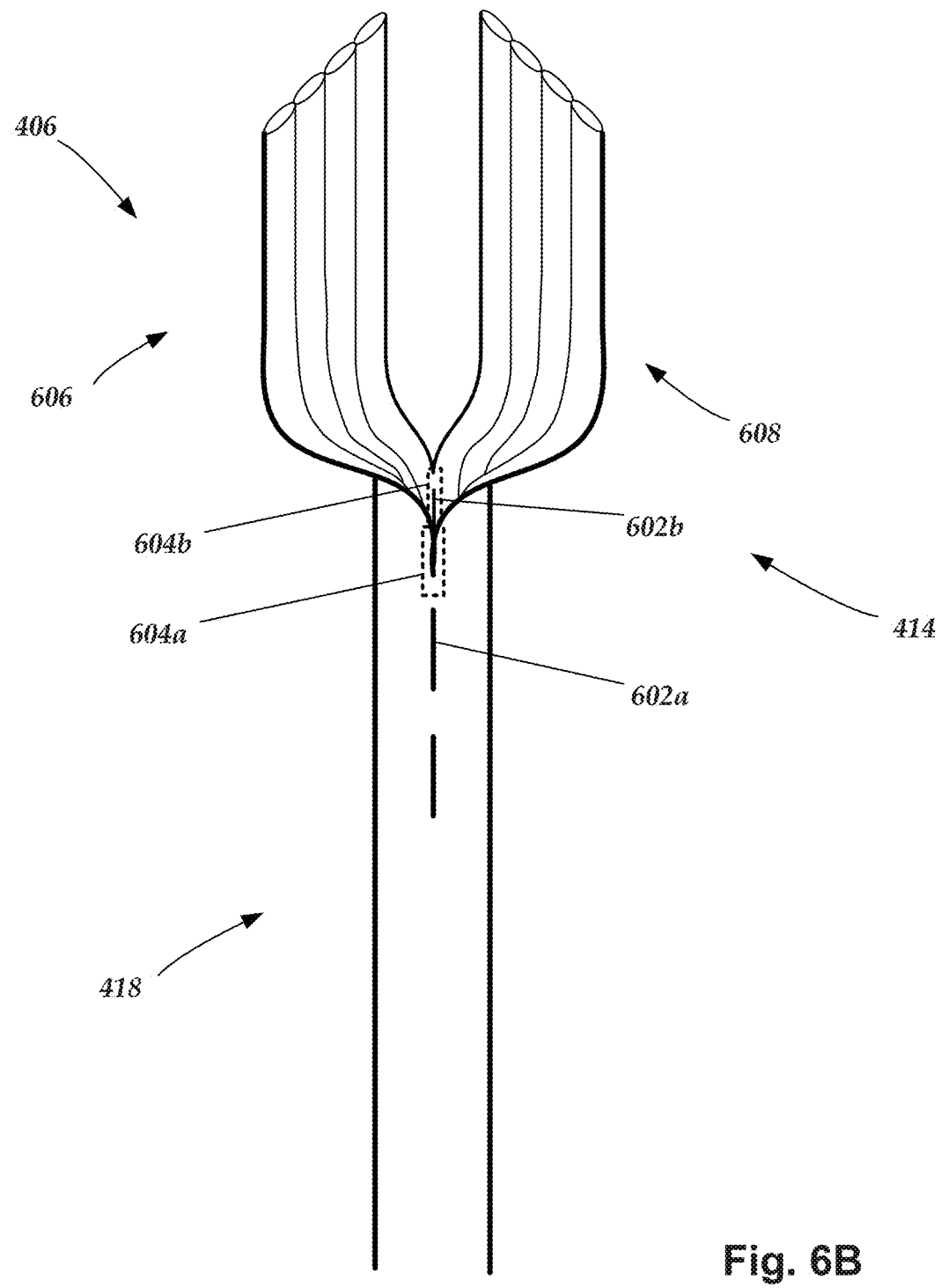
FIG. 6B is a schematic view of another embodiment of part of the cylindrical portion and part of the non-cylindrical portion of the lead body of FIG. 4C, the non-cylindrical portion having two non-cylindrical sections that are spaced apart from each other, according to the invention.

Examples of deploying the intermediate portion are illustrated in FIGS. 6A and 6B. FIG. 6A is a schematic view of one embodiment of part of the cylindrical portion 418 and part of the intermediate portion 414 of the lead 406. The intermediate portion 414 includes a separation element 602 that extends along a longitudinal dimension of the intermediate portion 414. In at least some embodiments, the separation element 602 may extend along at least 0.5, 1, 1.5, 2, 2.5, 3, 3.5, 4, 4.5, 5, 6, 7, 8, 9, or 10 centimeters or more of the length of the lead. In at least some embodiments, the separation element 602 extends along the entirety of the length of the lead 406. In other embodiments, the separation element 602 extends along only a portion of the length of the lead 406. For example, the separation element 602 may extend along the lead 406 through only the extension portion 412 and the intermediate portion 414 up to the distal electrode array 133. As another example, the separation element 602 extends along only the intermediate portion 414.

In at least some embodiments, prior to operation of the separation element 602, the separation element 602 may hold opposing longitudinal sides of the intermediate portion 414 together, thereby maintaining the intermediate portion 414 in a cylindrical configuration. Operation of the separation element 602 may deploy the intermediate portion 414 from the cylindrical configuration to the deployed configuration.

In at least some embodiments, the separation element 602 may include at least one registration structure (e.g., projections, depressions, chain, teeth, other zip-lock registration structures, or the like) disposed along one or both of the opposing sides of the intermediate portion 414. Registration of the registration structures with each other may hold the intermediate portion 414 in the cylindrical configuration. For example, the separation element 602 may include zipper chains or teeth disposed along the opposing sides of the intermediate portion 414. The lead 406 can include a mechanism for separation of the opposing sides of the intermediate portion 414 or a tool or other implement can be used to cause the separation.

In at least some embodiments, a slider 604 may be disposed between the opposing sides of the intermediate portion 414. Movement of the slider 604 along the length of the intermediate portion 414 may operate the separation element 602 to deploy the intermediate portion 414 from the cylindrical configuration to the deployed, non-cylindrical configuration. In at least some embodiments, the slider 604 may be external to a central lumen defined by the cylindrical configuration. In other embodiments, the slider 604 may be internal to the central lumen. In at least some embodiments, the separation element 602 may deploy the intermediate portion 414 from the cylindrical configuration to the deployed, non-cylindrical configuration responsive to movement of the slider 604 in a direction toward the distal end portion 410. In other embodiments, the separation element 602 may deploy the intermediate portion 414 to the deployed configuration responsive to movement of the slider 604 in a direction toward the extension portion 412. In at least some embodiments, the slider 604 may have a tab or other graspable feature. The tab or other graspable feature may be graspable by forceps such as, for example, micro forceps, thereby permitting the forceps to transfer a pulling or pushing force to the slider 604. In other embodiments, the slider 604 may have an aperture or opening into which an external tool such as a sickle probe, a screwdriver, a hex wrench, or the like may be inserted, thereby permitting the tool to move the slider 604.

In at least some embodiments, the slider 604 may include a blade so that moving the slider 604 may cut along the separation element 602 (for example, a cutting groove as discussed below), thereby causing the separation element 602 to deploy the intermediation portion 414 to the deployed, non-cylindrical configuration.

In at least some embodiments, the slider 604 may have a shape that increases the likelihood of pushing or pulling the slider 604 in a predetermined direction. For example, the slider 604 may have a ramping shape that has a lower height at one end portion of the slider 604 and that increases to a greater height at the other end portion of the slider 604. In at least some embodiments, the slider 604 may have a wall at the high end portion of the ramping shape. Accordingly, the ramp-shaped slider 604 may encourage a tool (for example, a stylet or the like) to gently pass over the slider 604 while the member travels in one direction and may encourage the member to, while the member travels in the other direction, catch (either a push or a pull) the end of the slider 604.

For example, while the separation element 602 maintains the intermediate portion 414 in the cylindrical configuration, the slider 604 may be disposed at the distal end portion of the separation element 602, in a central lumen defined by the cylindrical configuration, with the higher end facing the distal end portion 410 of the lead 406. In this case, the ramping shape of the slider 604 may encourage a stylet to gently pass over the slider 604 while the stylet is inserted through the intermediate portion 414 yet encourages the stylet to catch the end of the slider 604 as the stylet is removed (for example, the stylet may have a barb-shaped portion that catches the end of the slider 604). Alternatively, the slider 604 may be disposed at the extension portion 412 of the separation element 602 with a higher end on at least the proximal side of the slider 604, thereby encouraging a stylet to catch the slider 604 as the stylet extends toward the distal end portion 410 from inside the central lumen of the extension portion 412.

In at least some embodiments, the separation element 602 may be operated prior to insertion of a stylet into the lead 406. In other embodiments, the separation element 602 may be operated while inserting the stylet through the intermediate portion 414. In at least some embodiments, the separation element 602 may be operated while the stylet already extends through the lead 406 (either before or after implanting the lead 406). In at least some embodiments, the separation element 602 may be operated while removing the stylet from the lead 406 (for example, after implanting the lead 406). In other embodiments, the separation element 602 may be operated after removal of the stylet from the lead 406 (for example, after implanting the lead 406).

In at least some embodiments, the separation element 602 may include a pull strip. The pull strip may be disposed between the opposing sides of the intermediate portion 414 while holding the intermediate portion 414 in the cylindrical configuration. Pulling the pull strip away from the intermediate portion 414 may cause the pull strip to peel away from the opposing sides, thereby deploying the intermediate portion 414 to the deployed configuration. In at least some embodiments, at least one portion of the pull strip may extend beyond the opposing sides and hang free of the intermediate portion 414, thereby providing a gripping surface (for example, a tab or other graspable feature such as, for example, that discussed with regard to the slider 604) to initiate peeling the pull strip away from the intermediate portion 414. In at least some embodiments, pulling the pull strip toward the distal end portion 410 may deploy the intermediate portion 414 to the deployed configuration (for example, a portion of the pull strip may hang free of the intermediate portion 414 at the proximal end portion of the intermediate portion 414). Additionally or alternatively, pulling the pull strip toward the extension portion 412 may deploy the intermediate portion 414 to the deployed configuration (for example, a portion of the pull strip may hang free of the intermediate portion 414 at the distal end portion of the intermediate portion 414).

In at least some embodiments, the separation element 602 may include a cutting groove. The groove may define a path that, when cut, deploys the intermediate portion 414 from the cylindrical configuration to the deployed configuration. In at least some embodiments, the groove may guide a blade along the path. For example, the groove may include at least one indentation, perforation, pre-cut or pre-scored line, or the like. Additionally or alternatively, the groove may include a visual indicator such as, for example, a color-coded line. In at least some embodiments, a blade cutting along the path may cause the separation element 602 to deploy the intermediation portion 414 from the cylindrical configuration to the deployed configuration. In at least some embodiments, the blade may be an external blade (for example, a scalpel). In other embodiments, the blade may be attached to the intermediate portion 414 (for example, as explained in further detail below). In at least some embodiments, light such as, for example, light emitted by a laser may cut (for example, via heating) the separation element 602 to deploy the intermediate portion 414 from the cylindrical configuration to the deployed configuration.

In at least some embodiments, the separation element 602 may include at least one material that chemically reacts or dissolves to deploy the intermediate portion 414 to the deployed configuration. In at least some embodiments, the at least one material may be soluble in water, saline, or body fluids. For example, a solvent (for example, water or saline) may be applied to an interior of the intermediate portion 414 via injection (either before or after implanting the lead body) through the extension portion 412 of the lead body to cause separation at the intermediate portion. Additionally or alternatively, the at least one chemical may be applied to an exterior of the intermediate portion 414 (either before or after implanting the lead body). For example, the at least one chemical may be distributed into the implant location in the patient via a fluid flush subsequent to implanting the lead body. The at least one material of the separation element 602 may chemically react or dissolve responsive to the at least one chemical. Additionally or alternatively, the at least one material may chemically react or dissolve responsive to one or more body fluids at the implant location in the patient. In at least some embodiments, the at least one material may include salt or another mineral that dissolves into a liquid or other solvent (for example, water, a saline solution, or the like). Additionally or alternatively, the at least one material may include an adhesive (for example, water-based glue, cyanoacrylate glue, or the like) that dissolves into a liquid or other solvent (for example, biocompatible liquids or solvents). In at least some embodiments, light at a predetermined wavelength (for example, light from a laser or LED) may cause the separation element 602 to deploy the intermediate portion 414. For example, the separation element 602 may include at least one material that is sensitive to a specific wavelength or range of wavelengths of electromagnetic radiation.

FIG. 6B is a schematic view of another embodiment of part of the cylindrical portion and part of the intermediate portion 414 of the lead body of FIG. 4C. In the illustrated embodiment of FIG. 6B, the intermediate portion 414 includes at least two separation elements 602a, 602b with corresponding sliders 604a, 604b. In at least some embodiments, the separation elements 602a, 602b may have visual indicators that distinguish between each other (for example, the separation elements 602a, 602b may each be color coded with different colors). In at least some embodiments, the two separation elements 602a, 602b may be located on opposite sides of the intermediate portion 414 from each other. In at least some embodiments, the two separation elements 602a, 602b have the same length. In other embodiments, the two separation elements 602a, 602b have different lengths.

Prior to operation of the separation elements 602a, 602b, the separation elements 602a, 602b may hold opposing longitudinal sides of two sections 606, 608 together, thereby maintaining the intermediate portion 414 in the cylindrical configuration. Operation of one of the separation elements 602a, 602b deploys the intermediate portion 414 from the cylindrical configuration to the deployed configuration. Operation of the other one of the separation elements 602a, 602b causes the two sections 606, 608 to separate. In at least some embodiments, operation of both separation elements 602a, 602b may increase flexibility of the intermediate portion 414 in comparison to flexibility of the intermediate portion 414 when only one of the separation elements 602a, 602b have been operated.

In at least some embodiments, the two separation elements 602a, 602b are the same type of separation element 602 (for example, a slider, at least one chemically reactive material, at least one dissolving material, a registration structure, a cutting groove, a pull strip, or the like). In at least some embodiments, at least one of the separation elements 602a, 602b may be operated prior to insertion of a stylet into the lead 406. In other embodiments, at least one of the separation elements 602a, 602b may be operated while inserting the stylet through the intermediate portion 414. In at least some embodiments, at least one of the separation elements 602a, 602b may be operated while the stylet extends through the lead 406 (either before or after implanting the lead 406). In at least some embodiments, at least one of the separation elements 602a, 602b may be operated while removing the stylet from the lead 406. In other embodiments, at least one of the separation elements 602a, 602b may be operated after removal of the stylet from the lead 406.

Figure 7:
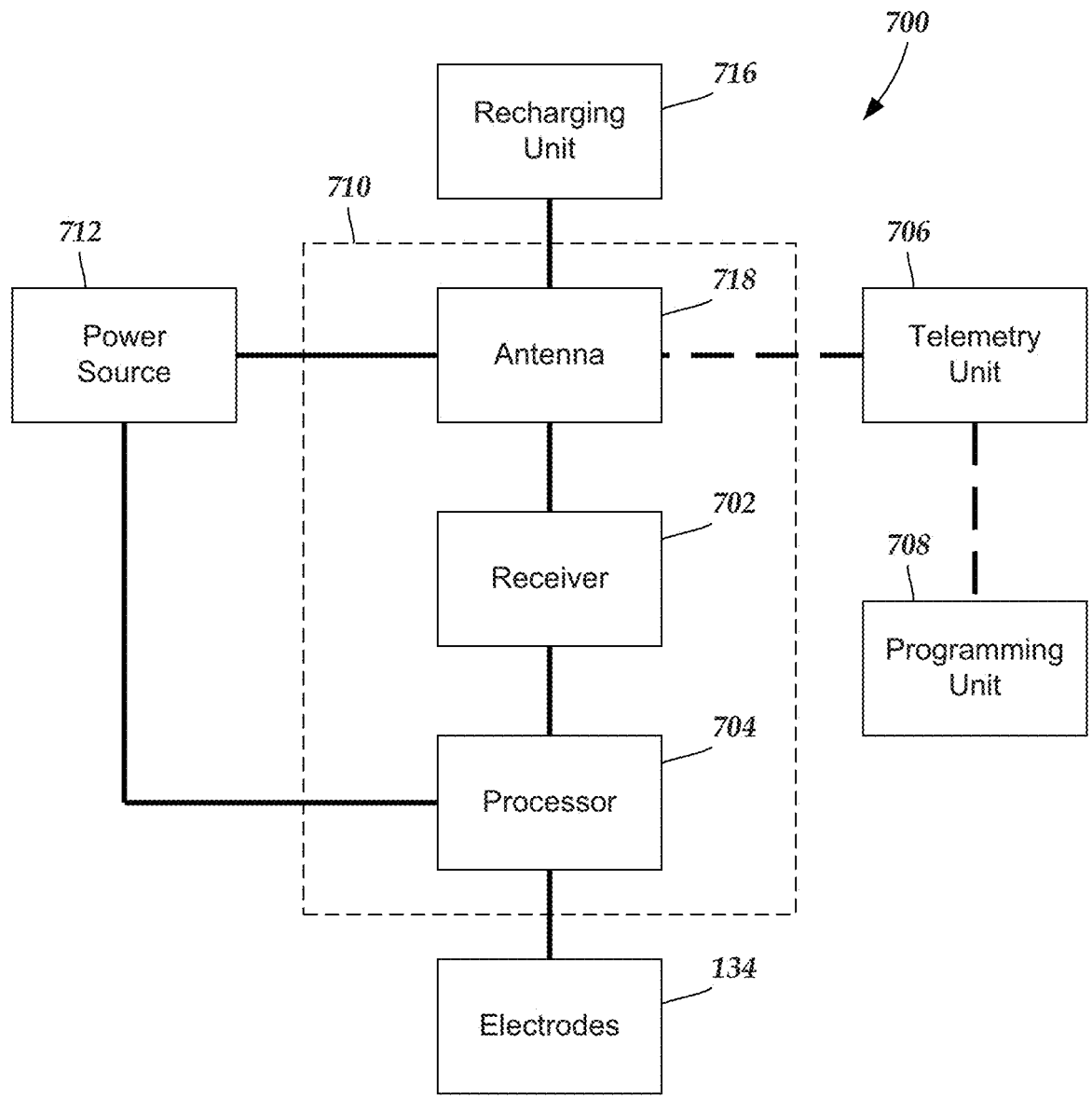
FIG. 7 is a schematic overview of one embodiment of components of an electrical stimulation system, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In at least some embodiments, the processor 704 may select which electrode(s) are cathodes and which electrode(s) are anodes. In at least some embodiments, the processor 704 may be used to identify which electrodes provide the most useful stimulation of the desired tissue.

Any processor can be used and can be as simple as an electronic device that, for example, produces pulses at a regular interval or the processor can receive and interpret instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
   a lead body having a distal end portion, a proximal end portion, and a longitudinal length;
   a plurality of terminals disposed along the proximal end portion of the lead body;
   a plurality of electrodes disposed along the distal end portion of the lead body; and
   a plurality of conductors extending along the lead body and electrically coupling the terminals to the electrodes;
   wherein the lead body comprises an intermediate portion disposed between the proximal end portion and the distal end portion, wherein the intermediate portion comprises at least one separation element that extends longitudinally along the intermediate portion, wherein the intermediate portion is deployable from an undeployed configuration to a deployed configuration responsive to operation of the at least one separation element, wherein, in the undeployed configuration, the intermediate portion defines a central lumen with the conductors arranged concentrically about the central lumen of the intermediate portion, wherein, in the deployed configuration, the intermediate portion defines at least one row of the conductors, wherein each of the at least one row comprises at least two of the conductors, wherein each of the at least one row is linear or arc-shaped when the intermediate portion is in the deployed configuration.

2. The lead of claim 1, wherein the at least one separation element comprises at least two separation elements, wherein the intermediate portion further comprises at least two sections that are separated from each other by the at least two separation elements, wherein the at least two sections, when the intermediate portion is in the deployed configuration, are spaced apart from each other.

3. The lead of claim 1, wherein the at least one separation element is configured and arranged for operation by a stylet inserted into the lead and into the intermediate portion to deploy the intermediate portion from the undeployed configuration to the deployed configuration.

4. The lead of claim 1, wherein the at least one separation element comprises at least one material configured and arranged, responsive to application of a chemical reactant, a solvent, or light having a predefined wavelength, to deploy the intermediate portion from the undeployed configuration to the deployed configuration.

5. The lead of claim 1, wherein the at least one separation element comprises a pull strip configured to peel away from opposing sides of the intermediate portion when pulled to deploy the intermediate portion from the undeployed configuration to the deployed configuration.

6. The lead of claim 1, wherein the at least one separation element comprises a cutting groove that defines a path that, when cut, deploys the intermediate portion from the undeployed configuration to the deployed configuration.

7. The lead of claim 1, wherein the at least one separation element comprises a series of perforations that defines a path for separation to deploy the intermediate portion from the undeployed configuration to the deployed configuration.

8. An electrical stimulation lead, comprising:
   a lead body having a distal end portion, a proximal end portion, and a longitudinal length;
   a plurality of terminals disposed along the proximal end portion of the lead body;
   a plurality of electrodes disposed along the distal end portion of the lead body; and
   a plurality of conductors extending along the lead body and electrically coupling the terminals to the electrodes;
   wherein the lead body comprises an intermediate portion disposed between the proximal end portion and the distal end portion, wherein the intermediate portion comprises at least one separation element that extends longitudinally along the intermediate portion, wherein the intermediate portion is deployable from an undeployed configuration to a deployed configuration responsive to operation of the at least one separation element, wherein the at least one separation element comprises a slider operable by sliding the slider to deploy the intermediate portion from the undeployed configuration to the deployed configuration.

9. The lead of claim 8, wherein the slider is configured and arranged to cut the intermediate portion as the slider is moved along the at least one separation element to separate opposing edges of the intermediate portion.

10. The lead of claim 8, wherein the slider is configured and arranged for grasping by a user or tool to operate the slider.

11. The lead of claim 8, wherein the slider is configured and arranged for receiving a portion of a tool to operate the slider using the tool.

12. An electrical stimulation system, comprising:
    the lead of claim 8; and
    a control module coupleable to the lead and comprising a housing and an electronic subassembly disposed in the housing.

13. The lead of claim 8, further comprising a stylet having a barb to catch the slider and move the slider along the intermediate portion to deploy the intermediate portion from the undeployed configuration to the deployed configuration.

14. An electrical stimulation system, comprising:
    the lead of claim 1; and
    a control module coupleable to the lead and comprising a housing and an electronic subassembly disposed in the housing.

15. An electrical stimulation lead, comprising:
    a lead body having a distal end portion, a proximal end portion, and a longitudinal length;
    a plurality of terminals disposed along the proximal end portion of the lead body;
    a plurality of electrodes disposed along the distal end portion of the lead body; and
    a plurality of conductors extending along the lead body and electrically coupling the terminals to the electrodes;
    wherein the lead body comprises a cylindrical portion and a non-cylindrical portion, wherein the cylindrical portion comprises the distal end portion and the proximal end portion and the non-cylindrical portion is disposed between the proximal end portion and the distal end portion, wherein, in the non-cylindrical portion, the conductors are arranged in at least one row, wherein each of the at least one row comprises at least two of the conductors and wherein each of the at least one row is linear or arc-shaped, wherein the cylindrical portion comprises a central lumen in both the proximal end portion and the distal end portion, wherein the cylindrical portion further comprises a plurality of first conductor lumens disposed concentrically around the central lumen, wherein part of the conductors are disposed in the first conductor lumens, wherein the non-cylindrical portion defines at least one row of second conductor lumens with the conductors extending through the second conductor lumens, wherein each of the at least one row of the second conductor lumens comprises at least two of the second conductor lumens, wherein each of the at least one row of the second conductor lumens is linear or arc-shaped, and a number of the second conductor lumens equals a number of the first conductor lumens.

16. The lead of claim 15, wherein the lead is configured and arranged to permit a stylet to extend from the central lumen of the proximal end portion to the central lumen of the distal end portion while the stylet bypasses the non-cylindrical portion.

17. The lead of claim 15, wherein the non-cylindrical portion further comprises a stylet lumen that permits a stylet to extend from the central lumen of the proximal end portion, through the stylet lumen of the non-cylindrical portion, to the central lumen of the distal end portion.

18. The lead of claim 17, wherein the stylet lumen is disposed in one of the at least one row.

19. The lead of claim 17, wherein the non-cylindrical portion defines an attachment element and the attachment element comprises the stylet lumen and is adjacent to at least one of the at least one row of the conductors.

20. An electrical stimulation system, comprising:
the lead of claim 15; and
a control module coupleable to the lead and comprising a housing and an electronic subassembly disposed in the housing.

* * * * *